United States Patent
Cong et al.

(10) Patent No.: US 12,071,612 B2
(45) Date of Patent: Aug. 27, 2024

(54) *LACTOBACILLUS GASSERI* HMV18 AND SECRETED PROTEIN AND APPLICATION THEREOF

(71) Applicant: HEBEI MEDICAL UNIVERSITY, Shijiazhuang (CN)

(72) Inventors: Bin Cong, Shijiazhuang (CN); Xianxian Jia, Shijiazhuang (CN)

(73) Assignee: Hebei Medical University, Shijiazhuang (CN)

( * ) Notice: Subject to any disclaimer, the term of this patent is extended or adjusted under 35 U.S.C. 154(b) by 376 days.

(21) Appl. No.: 17/246,365

(22) Filed: Apr. 30, 2021

(65) Prior Publication Data

US 2021/0371807 A1   Dec. 2, 2021

(30) Foreign Application Priority Data

May 6, 2020 (CN) .......................... 202010374100.6

(51) Int. Cl.
| | |
|---|---|
| *C12N 1/20* | (2006.01) |
| *C07K 14/335* | (2006.01) |
| *C12P 21/02* | (2006.01) |
| *A61K 38/00* | (2006.01) |
| *C12R 1/225* | (2006.01) |

(52) U.S. Cl.
CPC .............. *C12N 1/20* (2013.01); *C07K 14/335* (2013.01); *C12P 21/02* (2013.01); *A61K 38/00* (2013.01); *C12N 2500/02* (2013.01); *C12N 2500/12* (2013.01); *C12N 2500/16* (2013.01); *C12N 2500/30* (2013.01); *C12N 2500/32* (2013.01); *C12N 2500/34* (2013.01); *C12N 2500/46* (2013.01); *C12N 2500/74* (2013.01); *C12N 2500/84* (2013.01); *C12R 2001/225* (2021.05)

(58) Field of Classification Search
CPC ........................................................ C12N 1/20
See application file for complete search history.

(56) References Cited

U.S. PATENT DOCUMENTS

2020/0055905 A1*   2/2020   Madsen II ........... A61K 35/741

FOREIGN PATENT DOCUMENTS

WO   WO-2018089368 A1 *   5/2018   ........... A61K 35/741

OTHER PUBLICATIONS

Gao. A new Lactobacillus gasseri strain HMV18 inhibits the growth of pathogenic bacteria. Food Science and Human Wellness, vol. 11, Issue 2, 2022, pp. 247-254.*

* cited by examiner

*Primary Examiner* — Yong D Pak
(74) *Attorney, Agent, or Firm* — Leason Ellis LLP

(57) ABSTRACT

The present disclosure relates to the technical field of microorganisms, in particular to *Lactobacillus gasseri* HMV18 and a secreted protein and an application thereof. The *Lactobacillus gasseri* HMV18 is preserved in the China Center for Type Culture Collection on Jul. 11, 2019 with a preservation number of CCTCC NO: M 2019538, and a preservation address of Wuhan University, Wuhan, China. The protein extracted from the *Lactobacillus gasseri* HMV18 has antibacterial and anti-tumor effects, but basically has no effect on normal myocardial cells, so the *Lactobacillus gasseri* HMV18 can be applied to preparation of antibacterial and anti-tumor products.

4 Claims, 12 Drawing Sheets

Specification includes a Sequence Listing.

1. *Lactobacillus salivarius* (*L. salivarius* 11741)
2. *Lactobacillus rhamnosus* (*L. rhamnosus*)
3. *Lactobacillus fermentum* (*L. fermentum*)
4. *L. gasseri* HMV18
5. *L. salivarias* F1

Table 1. Biochemical test of *L. gasseri*

| Biochemical test | Reaction | Biochemical test | Reaction |
|---|---|---|---|
| (AMY) D-Amygdalin[a] | - | (POLYB) Polymixin B Resistance[a] | - |
| (PIPLC) Phosphatidylinositol Phospholipase C[a] | - | (dGAL) D-Galactose[a] | - |
| (dXYL) D-Xylose[a] | - | (dRIB) D-Ribose[a] | - |
| (ADH 1) Arginine Dihydrolase 1[a] | + | (lLATk) L-Lactate Alkalinization[a] | - |
| (BGAL) β-D-Galactosidase[a] | - | (LAC) Lactose[ab] | + |
| (AGLU) α-Glucosidase[a] | - | (NAG) N-Acetyl-D-Glucosamine[a] | + |
| (APPA) Ala-Phe-Pro Arylamidase[a] | - | (dMAL) D-Maltose[ab] | + |
| (CDEX) Cyclodextrin[a] | - | (BACI) Bacitracin Resistance[a] | + |
| (AspA) L-aspartate Arylamidase[a] | - | (NOVO) Novobiocin Resistance[a] | + |
| (BGAR) β-Galactopyranosidase[a] | - | (NC6.5) Growth In 6.5% NaCl[a] | + |
| (AMAN) α-Mannosidase[a] | - | (dMAN) D-Mannitol[ab] | - |
| (PHOS) Phosphatase[a] | - | (dMNE) D-Mannose[a] | + |
| (LeuA) Leucine Arylamidase[a] | + | (MBdG) Methyl-B-D-Glucopyranoside[a] | - |
| (ProA) L-proline Arylamidase[a] | - | (PUL) Pullulan[a] | - |
| (BGURr) β-Glucuronidase[a] | - | (dRAF) D-Raffinose[ab] | + |
| (AGAL) α-Galactosidase[a] | - | (Comp.Vibrio.)[a] | - |
| (PyrA) Pyroglutaminase[a] | - | (SAL) Salicin[ab] | + |
| (BGUR) β-D-Glucuronidase[a] | - | (SAC) Saccharose/Sucrose[ab] | + |
| (AlaA) Alanine Arylamidase[a] | + | (dTRE) D-Trehalose[a] | - |
| (TyrA) Tyrosine Arylaminase[a] | - | (ADH2s) Arginine Dihydrolase 2[a] | - |
| (dSOR) D-Sorbitol[ab] | - | (OPTO) Optochin Resistance[a] | + |
| (URE) Urease[a] | - | (SYN) Synanthrin[b] | + |
| (AES) Aescin[b] | - | (dCEL) D-Cellobiose[b] | + |
| (SH) Sodium Hippurate[b] | - | | |

Fig. 22

SEQUENCE LISTING

<160> NUMBER OF SEQ ID NOS: 2

<210> SEQ ID NO 1
<211> LENGTH: 1161
<212> TYPE: DNA
<213> ORGANISM: LACTOBACILLUS GASSERI

<400> SEQUENCE: 1

```
gcggggcggg gtgctataca tgcagtcgag cgagcttgcc tagatgaatt tggtgcttgc      60
accaaatgaa actagataca agcgagcggc ggacgggtga gtaacacgtg ggtaacctgc     120
ccaagagact gggataacac ctggaaacag atgctaatac cggataacaa cactagacgc     180
atgtctagag tttaaaagat ggttctgcta tcactcttgg atggacctgc ggtgcattag     240
ctagttggta aggtaacggc ttaccaaggc aatgatgcat agccgagttg agagactgat     300
cggccacatt gggactgaga cacggcccaa actcctacgg gaggcagcag tagggaatct     360
tccacaatgg acgcaagtct gatggagcaa cgccgcgtga gtgaagaagg gtttcggctc     420
gtaaagctct gttggtagtg aagaaagata gaggtagtaa ctggcctttt tttgacggta     480
attacttaga aagtcacggc taactacgtg ccagcagccg cggtaatacg taggtggcaa     540
gcgttgtccg gatttattgg gcgtaaagcg agtgcaggcg gttcaataag tctgatgtga     600
aagccttcgg ctcaaccgga gaattgcatc agaaactgtt gaacttgagt gcagaagagg     660
agagtggaac tccatgtgta gcggtggaat gcgtagatat atggaagaac accagtggcg     720
aaggcggctc tctggtctgc aactgacgct gaggctcgaa agcatgggta gcgaacagga     780
ttagataccc tggtagtcca tgccgtaaac gatgagtgct aagtgttggg aggtttccgc     840
ctctcagtgc tgcagctaac gcattaagca ctccgcctgg ggagtacgac cgcaaggttg     900
aaactcaaag gaattgacgg gggcccgcac aagcggtgga gcatgtggtt taattcgaag     960
caacgcgaag aaccttacca ggtcttgaca tccagtgcaa acctaagaga ttaggagttc    1020
ccttcgggac gctgaaacag gtgtgcatgg ctgtcgtcag ctcgggcctg gaatgttggg    1080
ttaagtcccg aacgaggcaa ccttgcctta attgcctcct taagttgggc ctctaatgaa    1140
atgccgggga aaaccgaaga a                                              1161
```

<210> SEQ ID NO 2
<211> LENGTH: 64
<212> TYPE: DNA
<213> ORGANISM: LACTOBACILLUS GASSERI

<400> SEQUENCE: 2

```
cacctggaaa cagatgctaa taccggataa caacactaga cgcatgtcta gagtttaaaa      60
gatg                                                                    64
```

LACTOBACILLUS GASSERI HMV18 AND SECRETED PROTEIN AND APPLICATION THEREOF

CROSS-REFERENCE TO RELATED APPLICATIONS

This application claims priority to Chinese Patent Application No. CN 202010374100.6, filed on May 6, 2020, which is hereby incorporated herein by reference in its entirety.

SEQUENCE LISTING

The application contains a Sequence Listing which has been submitted electronically in ASCII format and is hereby incorporated by reference in its entirety. Said ASCII copy, created on Dec. 11, 2023, is named 11300_010133-US0_ST25-V2.txt and is 2,209 bytes in size.

TECHNICAL FIELD

The present disclosure relates to the technical field of microorganisms, and in particular to a *Lactobacillus gasseri* HMV18 and a secreted protein and an application thereof.

BACKGROUND

Bacteria are one of the main groups of organisms. For human beings, there are both beneficial bacteria and pathogenic bacteria. Bacterial infections may occur when pathogenic bacteria invade in a blood circulation, and grow and reproduce. Especially for the elderly, children and people with chronic diseases or a low immune function, an improper treatment, a delayed treatment or an accompanying complication after bacterial infection will cause septicemia or pyemia. For example, *Escherichia coli* belongs to Enterobacteriaceae, parasitizes large intestine and small intestine of a human body, is resident flora in the human body, is harmless to health of the human body under a normal condition, and can defense pathogenic bacteria and assist in synthesis of Vitamin B group, Vitamin K2, etc. When special cases, such as, reduced immune function of the organism and lack of enteral stimulation, occur, it may cause *Escherichia coli* to parasitize urethra, gall bladder, urinary bladder, epityphlon or other parts, thereby making *Escherichia coli* pathogenic bacteria, and leading to an infection on the corresponding part, or even causing a systemic infection. In addition, the pathogenic bacteria in *Escherichia coli* in vitro may further induce food poisoning to the human body, or cause diarrhea in animals such as pigs, cows and sheep, which brings serious harm to the livestock industry.

In the prior art, antibiotics are used to prevent bacterial infection mostly. However, the extensive use of the antibiotics leads to continuous increase of antibiotic resistant bacteria. Therefore, there is an urgent need for an antibacterial material other than the antibiotics to inhibit bacteria proliferation.

In another aspect, the incidence of malignant tumors in China has been increasing significantly and in recent years the population of people with this disease has been relatively younger. At present, tumor therapies include a surgical resection, a radiotherapy, a chemotherapy and a biotherapy. The surgical resection has a variety of inapplicable circumstances, such as a systemic malignant tumor, multiple metastases, accompanying severe heart and lung diseases, and may further cause a surgical complication. The radiotherapy is inapplicable for tumors with a low radio sensitivity such as osteosarcoma, fibrosarcoma, liposarcoma and rhabdomyosarcoma, and is always accompanied with side effects such as nausea and vomiting, fever, a damage to a hematopoietic system, a damage to skin and hair loss. For most tumors, the chemotherapy cannot cure them completely and other therapies such as surgery and the radiotherapy are needed; moreover, the chemotherapy has damage to the normal tissue, may cause myelosuppression, decrease of white blood cells and platelets, nausea and vomiting, a damage to hepar and renal functions, immunosuppression, and develops drug resistance. The biotherapy may also cause side effects due to too strong immunity during treatment, such as high fever and nausea. Due to complicated biological characteristics of solid tumors, an immunotherapy in the biological has not yet reached a stage of accurate killing of cancer cells, and there is a severe off-target effect in the treatment of the solid tumors, which may cause damage to the normal tissue or cells.

In view of the defects in the current tumor therapies, there is an urgent need for a novel therapy with a clear curative effect, low drug resistance, safety and reliability, slight toxic and side effects, and the ability to improve an anti-tumor immune function of tumor patients.

SUMMARY

These and other problems are generally solved or circumvented, and technical advantages are generally achieved, by embodiments of the present disclosure which provide a *Lactobacillus gasseri* HMV18 and a secreted protein and an application thereof.

Technical Problems

Aiming at the technical problems such as continuous increase of antibiotic resistant bacteria caused by excessive use of antibiotics, and large side effects and poor targeting ability of the current oncotherapy, the present disclosure provides *Lactobacillus gasseri* HMV18.

And, the present disclosure further provides a culture method of the *Lactobacillus gasseri* HMV18.

And, the present disclosure further provides a secreted protein of *Lactobacillus gasseri*.

And, the present disclosure further provides a preparation method of a secreted protein of the *Lactobacillus gasseri*.

And, the present disclosure further provides an application of the secreted protein of the *Lactobacillus gasseri* in preparation of an antibacterial product.

And, the present disclosure further provides an application of a secreted protein of the *Lactobacillus gasseri* prepared by the preparation method in preparation of an antibacterial product.

And, the present disclosure further provides an application of the secreted protein of the *Lactobacillus gasseri* in preparation of an anti-tumor product.

And, the present disclosure further provides an application of a secreted protein of the *Lactobacillus gasseri* prepared by the preparation method in preparation of an anti-tumor product.

Technical Solutions

In order to achieve the purposes of the invention, the present disclosure adopts the following technical solutions:

The *Lactobacillus gasseri* HMV18, with a systematic name of *Lactobacillus gasseri*, is preserved in China Center for Type Culture Collection on Jul. 11, 2019 with a preservation number of CCTCC NO: M 2019538, and a preservation address of Wuhan University, Wuhan, China.

The *Lactobacillus gasseri* HMV18 provided by the present disclosure is obtained by separating from a healthy woman's vagina and screening, belongs to *Lactobacillus*, has no toxicity, no pollution, no carcinogenicity and no pathogenicity, does not damage a normal tissue, does not contain drug resistant plasmids, and does not cause horizontal transmission resistance. A protein component secreted by the *Lactobacillus gasseri* HMV18 can inhibit growth and reproduction of pathogenic bacteria such as *Escherichia coli*, *Staphylococcus aureus* and *Klebsiella oxytoca*. Moreover, when acting on a tumor cell line in vitro, the protein component can cause leakage of a tumor cell membrane within 40 min, and has a significant oncolytic effect. In vivo tests also proves that the secreted protein of the *Lactobacillus gasseri* HMV18 obviously inhibits growth of a tumor in an animal model transplanted with a tumor, and can activate humoral immunity and cellular immunity of an organism so that the organism produces cytokines such as a tumor necrotic factor, interferon and interleukin, and anti-tumor immune response of the organism is improved. A solid tumor has a low oxygen metabolism area, the *Lactobacillus gasseri* HMV18 reproduces under an anaerobic condition, and has a characteristic of chemotaxis to the low oxygen metabolism area, the *Lactobacillus gasseri* HMV18 is subcutaneously injected into a mouse for safety evaluation, and no obvious pathological change is found, so that the *Lactobacillus gasseri* HMV18 has a good targeting to the solid tumor, can play a role in resisting the solid tumor by producing metabolite with anti-tumor activity, inhibit tumor cell proliferation, improve tumor cell apoptosis or directly cause the leakage of the tumor cell membrane to play an oncolytic effect, and can be used in tumor therapies or used as a transfer vector for a tumor gene therapy.

A method for screening strains of the *Lactobacillus gasseri* HMV18 specifically includes the following steps:

(1) Specimen Collection

Collecting vaginal secretions of 100 women at the childbearing age of 25-45 who did not take antibiotics within the last 1 month and did not have a medical history of a malignant disease, infectious disease or metabolic disease such as cancer, Hepatitis B, Hepatitis C, syphilis and Aids, and diabetes, numbering the collected vaginal secretions, and respectively inoculating the numbered vaginal secretions to improved de Man, Rogosa and Sharpe (MRS) liquid media (including the following raw materials in parts by weight: 10 parts of tryptone, 10 parts of beef extract, 5 parts of yeast extract, 20 parts of raffinose, 5 parts of sodium acetate, 2 parts of diamine citrate, 1 part of tween 80, 2 parts of dipotassium phosphate, 0.05 part of manganese sulfate, 0.5 part of magnesium sulfate and 1,000 parts of double distilled water, and being sterilized with high-pressure vapor at 121° C. for 20 min), culturing the inoculated improved MRS liquid media in a thermostatic incubator at 37° C. for 24 hours (h) under an anaerobic condition to obtain incubated clinical samples I, centrifuging the clinical samples I at 4,000 revolutions per minute (r/min) for 15 min, separating supernates and precipitates from the clinical samples I, freezing the supernates in a refrigerator at −20° C. for later use (total 100 parts of supernates), and freezing the precipitates in a refrigerator at −20° C. for antibacterial identification and separation (total 100 parts of precipitates).

(2) Antibacterial Test

Respectively inoculating *Escherichia coli* (*E. Coli*), *Klebsiella oxytoca* (*K. oxytaca*) and *Staphylococcus aureus* (*S. aureus*) to Luria-Bertani (LB) plate media by using a streak inoculation method, culturing the inoculated LB plate media at 37° C. for 18 h, and respectively resuscitating the *Escherichia coli* (*E. Coli*), the *Klebsiella oxytoca* (*K. oxytaca*) and the *Staphylococcus aureus* (*S. aureus*) to obtain single colonies. Picking and inoculating the single colonies to an LB liquid medium, culturing the inoculated LB liquid medium at 37° C. for 24 h, and centrifuging the LB liquid medium at 5,000 r/min for 10 min to obtain a bacteria precipitate I. Diluting the bacteria precipitate I with normal saline to $1\times10^9$ colony-forming units per milliliter (CFU/mL) to obtain a bacteria precipitate II, where at this time a spectro-photometer reads that optical density 600=1 ($OD_{600}=1$), and then diluting the bacteria precipitate II with normal saline to prepare a bacteria suspension I at a concentration of 105 CFU/mL. Sucking up 0.1 mL of the diluted bacteria suspension I, and uniformly coating the bacteria suspension I onto an LB solid medium by using sterile glass beads. Uniformly placing 100 Oxford cups on the LB solid medium coated with the bacteria suspension I, respectively adding the supernates of the 100 clinical samples I obtained at step (1) into the Oxford cups according to 0.2 mL of the supernates per Oxford cup, allowing the LB solid medium to absorb the supernates at 4° C. for 24 h, and then incubating the LB solid medium in an incubator at 37° C. to obtain 100 clinical samples II. After 24 h, finding colonies which can inhibit the *Escherichia coli* (*E. Coli*), the *Klebsiella oxytoca* (*K. oxytaca*) and the *Staphylococcus aureus* (*S. aureus*) in the supernates of 56 clinical samples II.

(3) Separation

Inoculating precipitates corresponding to the supernates obtained at (2) which may inhibit the *Escherichia coli*(*E. Coli*), the *Klebsiella oxytoca* (*K. oxytaca*) and the *Staphylococcus aureus* (*S. aureus*) to an improved MRS agar medium (including the following raw materials in parts by weight: 10 parts of tryptone, 10 parts of beef extract, 5 parts of yeast extract, 20 parts of raffinose, 5 parts of sodium acetate, 2 parts of diamine citrate, 1 part of tween 80, 2 parts of dipotassium phosphate, 0.05 part of manganese sulfate, 0.5 part of magnesium sulfate, 1,000 parts of double distilled water, 15 parts of agar and 0.5 part of L-cysteine hydrochloride, and being sterilized with high-pressure vapor at 121° C. for 20 min) by using a streak inoculation method. Activating the inoculated improved MRS agar medium at 37° C. for 72 h under an anaerobic condition, picking smooth white colonies, carrying out streak purification on the smooth white colonies twice, and transferring the smooth white colonies into an MRS liquid medium to obtain a smooth white colony culture solution, and culturing the smooth white colony culture solution under an anaerobic condition at 37° C. to obtain *Lactobacillus*. Identifying the obtained *Lactobacillus*.

And, an embodiment of the present disclosure further provides a culture method of the *Lactobacillus gasseri* HMV18, including the following steps: culturing the *Lactobacillus gasseri* HMV18 by using an improved MRS agar medium under an anaerobic condition at a constant temperature of 37° C., where the improved MRS agar medium includes the following raw materials in parts by weight: 10 parts of tryptone, 10 parts of beef extract, 5 parts of yeast extract, 20 parts of raffinose, 5 parts of sodium acetate, 2 parts of diamine citrate, 1 part of tween 80, 2 parts of dipotassium phosphate, 0.05 part of manganese sulfate, 0.5 part of magnesium sulfate, 1,000 parts of double distilled water, 15 parts of agar and 0.5 part of L-cysteine hydrochloride. The improved MRS medium has different effects on proliferation of different bacteria, so that the *Lactobacillus gasseri* HMV18 has a morphological difference from other bacteria and can be screened and separated.

And, an embodiment of the present disclosure further provides a culture method of the *Lactobacillus gasseri* HMV18, including the following steps: culturing the *Lactobacillus gasseri* HMV18 by using an improved MRS liquid medium under an anaerobic condition at a constant temperature of 37° C., where the improved MRS liquid medium includes the following raw materials in parts by weight: 10 parts of tryptone, 10 parts of beef extract, 5 parts of yeast extract, 20 parts of raffinose, 5 parts of sodium acetate, 2 parts of diamine citrate, 1 part of tween 80, 2 parts of dipotassium phosphate, 0.05 part of manganese sulfate, 0.5 of magnesium sulfate and 1,000 parts of double distilled water. The method can achieve proliferation of the *Lactobacillus gasseri* HMV18.

And, an embodiment of the present disclosure further provides a secreted protein of *Lactobacillus gasseri*, where the secreted protein of the *Lactobacillus gasseri* is extracted from the *Lactobacillus gasseri* HMV18, and is a secreted protein of the *Lactobacillus gasseri* HMV18.

And, an embodiment of the present disclosure further provides a preparation method of a secreted protein of *Lactobacillus gasseri*, specifically including the following steps:
  at step a, culturing the *Lactobacillus gasseri* HMV18 under an anaerobic condition, and subculturing the *Lactobacillus gasseri* HMV18 to obtain a second-generation bacteria solution;
  at step b, centrifuging the second-generation bacteria solution at 5,000 rpm for 10 min, and removing a precipitate to obtain a supernate I;
  at step c, adding 1 mole per liter (mol/L) sodium hydroxide (NaOH) and 1 mol/L catalase into the supernate I to obtain a mixture I and regulate a pH value of the mixture I to be 6.2, stirring the mixture I at 4° C. for 2 h, allowing the mixture I to stand for 2 h, centrifuging the mixture I at 4° C. at 12,000 rpm for 30 min, removing a precipitate to obtain a supernate II;
  at step d, adding ammonium sulfate into the supernate II to obtain a mixture II, stirring the mixture II at 4° C. for 2 h, allowing the mixture II to stand for 10 h, centrifuging the mixture II at 4° C. at 12,000 rpm for 30 min to obtain a centrifuged product, and removing a supernate from the centrifuged product, and collecting a precipitated protein to obtain the secreted protein of the *Lactobacillus gasseri*.

According the preparation method, impurities in the supernate I are removed by means of catalase treatment and pH regulation, and ammonium sulfate can precipitate the target protein, so that the obtained secreted protein of the *Lactobacillus gasseri* has more obvious antibacterial and anti-tumor effects compared to the *Lactobacillus gasseri* HMV18, has a significant effect in inhibiting *Escherichia coli, Staphylococcus aureus* and *Klebsiella oxytoca*, can induce apoptosis of tumor cells such as a human cervical cancer cell Hela, a human ovary carcinoma cell SHIN3, a human lung adenocarcinoma cell A549, a human chondrosarcoma cell SW1353, a human hepatocarcinoma cell HepG2, a human bone marrow neuroblastoma cell SH-SY5Y and a melanoma cell B16-OVA, and has no obvious effect on myocardial cells.

Preferably, the method for culturing the *Lactobacillus gasseri* HMV18 under an anaerobic condition in step a includes: culturing the *Lactobacillus gasseri* HMV18 under an anaerobic condition at a constant temperature of 37° C. by using an improved MRS liquid medium, where the improved MRS liquid medium includes the following raw materials in parts by weight: 10 parts of tryptone, 10 parts of beef extract, 5 parts of yeast extract, 20 parts of raffinose, 5 parts of sodium acetate, 2 parts of diamine citrate, 1 part of tween 80, 2 parts of dipotassium phosphate, 0.05 part of manganese sulfate, 0.5 part of magnesium sulfate and 1,000 parts of double distilled water.

Preferably, the step d further includes a step of dialysing and purifying the centrifuged product.

And, an embodiment of the present disclosure further provides an application of the secreted protein of the *Lactobacillus gasseri* in preparation of an antibacterial product, where active ingredients in the antibacterial product include the secreted protein of *Lactobacillus gasseri*. The secreted protein of the *Lactobacillus gasseri* can inhibit growth and reproduction of pathogenic bacteria such as *Escherichia coli, Staphylococcus aureus* and *Klebsiella oxytoca*, and does not develop a drug resistance.

And, an embodiment of the present disclosure further provides an application of a secreted protein of the *Lactobacillus gasseri* prepared by the preparation method of the secreted protein of the *Lactobacillus gasseri* in preparation of an antibacterial product.

And, an embodiment of the present disclosure further provides an application of the secreted protein of the *Lactobacillus gasseri* in preparation of an anti-tumor product. The protein can induce apoptosis of tumor cells such as a human cervical cancer cell line (Hela cells), a human ovary carcinoma cell line (SHIN3 cells), a human lung adenocarcinoma cell line (A549 cells), a human chondrosarcoma cell line (SW1353 cells), a human hepatocarcinoma cell line (HepG2 cells), a human bone marrow neuroblastoma cell line (SH-SY5Y cells) and a murine melanoma cell line (B16-OVA cells), and has no obvious effect on myocardial cells.

And, an embodiment of the present disclosure further provides an application of a secreted protein of the *Lactobacillus gasseri* prepared by the preparation method of the secreted protein of the *Lactobacillus gasseri* in preparation of an anti-tumor product.

The foregoing has outlined rather broadly the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

FIG. 22 shows the Table 1 Biochemical Identification of the *Lactobacillus gasseri* HMV18.

Corresponding numerals and symbols in the different figures generally refer to corresponding parts unless otherwise indicated. The figures are drawn to clearly illustrate the relevant aspects of the various embodiments and are not necessarily drawn to scale.

DETAILED DESCRIPTION OF ILLUSTRATIVE EMBODIMENTS

Figure 1:
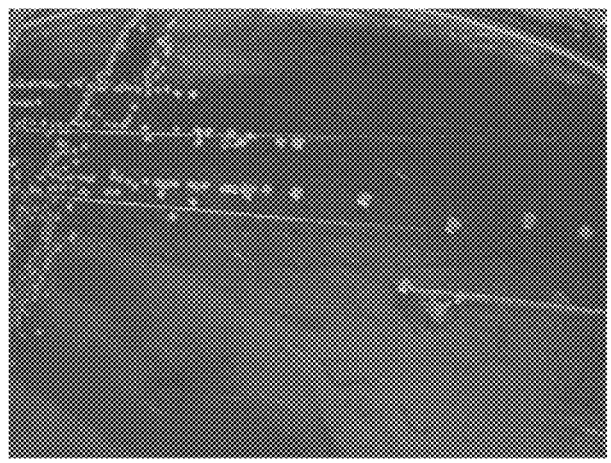
FIG. 1 shows colony morphology of the *Lactobacillus gasseri* HMV18 in an improved MRS solid medium of Embodiment 1 of the present disclosure.

In order to make objects, technical solutions and advantages of the present disclosure clearer, the present disclosure will be further described in details below in conjunction with the accompanying drawings. It should be understood that the description herein is only used to explain the present disclosure, and is not used to limit the present disclosure.

Embodiment 1

The embodiment of the present disclosure provides procedures for screening and identifying the *Lactobacillus gasseri* HMV18:

1. Separation and Purification of the *Lactobacillus gasseri* HMV18

1.1 Specimen Collection

Collecting vaginal secretions of 100 women at the childbearing age of 25-45 who did not take antibiotics within the last 1 month and did not have a medical history of a malignant disease, infectious disease or metabolic disease such as cancer, Hepatitis B, Hepatitis C, syphilis and Aids, and diabetes, numbering the collected vaginal secretions, and respectively inoculating the numbered vaginal secretions to improved de Man, Rogosa and Sharpe (MRS) liquid media (including the following raw materials: 10 gram (g) of tryptone, 10 g of beef extract, 5 g of yeast extract, 20 g of raffinose, 5 g of sodium acetate, 2 g of diamine citrate, 1 g of tween 80, 2 g of dipotassium phosphate, 0.05 g of manganese sulfate, 0.5 g of magnesium sulfate and 1 L of double distilled water, and being sterilized with high-pressure vapor at 121° C. for 20 min), culturing the inoculated improved MRS liquid media in a thermostatic incubator at 37° C. for 24 hour (h) under an anaerobic condition to obtain incubated clinical samples I, centrifuging the clinical samples I at 4,000 r/min for 15 min, separating supernate sand precipitates from the clinical samples I, freezing the supernates in a refrigerator at −20° C. for later use (total 100 parts of supernates), and freezing the precipitates in a refrigerator at −20° C. for antibacterial identification and separation (total 100 parts of precipitates).

1.2 Antibacterial Test

Respectively inoculating *Escherichia coli* (*E. Coli*), *Klebsiella oxytoca* (*K. oxytaca*) and *Staphylococcus aureus* (*S. aureus*) to LB plate media by using a streak inoculation method, culturing the inoculated LB plate media at 37° C. for 18 h, and respectively resuscitating the *Escherichia coli* (*E. Coli*), the *Klebsiella oxytoca* (*K. oxytaca*) and the *Staphylococcus aureus* (*S. aureus*) to obtain single colonies. Picking and inoculating the single colonies to an LB liquid medium, culturing the inoculated LB liquid medium at 37° C. for 24 h, and centrifuging the LB liquid medium at 5,000 r/min for 10 min to obtain a bacteria precipitate I. Diluting the bacteria precipitate I with normal saline to 1×10⁹ CFU/mL to obtain a bacteria precipitate II, where at this time a spectro-photometer read that $OD_{600}=1$, and then diluting the bacteria precipitate II with normal saline to prepare a bacteria suspension I at a concentration of 105 CFU/mL. Sucking up 0.1 mL of the diluted bacteria suspension I, and uniformly coating the bacteria suspension I onto an LB solid medium by using sterile glass beads. Uniformly placing 100 Oxford cups on the LB solid medium coated with the bacteria suspension I, respectively adding the supernates of the 100 clinical samples I obtained at step (1) into the Oxford cups according to 0.2 mL of the supernate per Oxford cup, allowing the LB solid medium to absorbed the supernates at 4° C. for 24 h, and then incubating the LB solid medium in an incubator at 37° C. to obtain 100 clinical samples II, and inhibiting effects on the *Escherichia coli* (*E. Coli*), the *Klebsiella oxytoca* (*K. oxytaca*) and the *Staphylococcus aureus* (*S. aureus*) of the 100 clinical samples II were respectively observed. After 24 h, colonies which may inhibit the *Escherichia coli* (*E. Coli*), the *Klebsiella oxytoca* (*K. oxytaca*) and the *Staphylococcus aureus* (*S. aureus*) were found in the supernates of 56 clinical samples II.

1.3 Separation

Inoculating precipitates corresponding to the supernates obtained at 1.2 which may inhibit the *Escherichia coli* (*E. Coli*), the *Klebsiella oxytoca* (*K. oxytaca*) and the *Staphylococcus aureus* (*S. aureus*) to an improved MRS agar medium by using a streak inoculation method. Where the improved MRS agar medium included the following raw materials in parts by weight: 10 parts of tryptone, 10 parts of beef extract, 5 parts of yeast extract, 20 parts of raffinose, 5 parts of sodium acetate, 2 parts of diamine citrate, 1 part of tween 80, 2 parts of dipotassium phosphate, 0.05 part of manganese sulfate, 0.5 part of magnesium sulfate, 1,000 parts of double distilled water, 15 parts of agar and 0.5 part of L-cysteine hydrochloride, and being sterilized with high-pressure vapor at 121° C. for 20 min. Activating the inoculated improved MRS agar medium at 37° C. for 72 h under an anaerobic condition, picking smooth white colonies, carrying out streak purification on the smooth white colonies twice, and transferring the smooth white colonies into an MRS liquid medium to obtain a smooth white colony culture solution, and culturing the smooth white colony culture solution at 37° C. under an anaerobic condition to obtain *Lactobacillus*. Identifying the obtained *Lactobacillus*.

2. Identifications 2.1 Gram Staining

Figure 2:
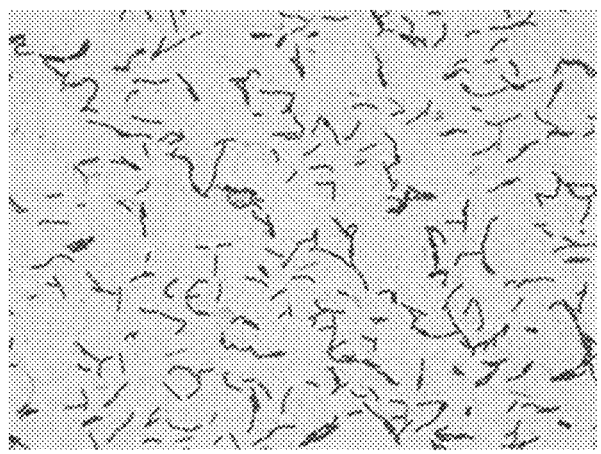
FIG. 2 shows a result of Gram staining of the *Lactobacillus gasseri* HMV18 of the Embodiment 1 of the present disclosure.

The smooth white colony culture solution obtained at 1.3 was smeared, dried, fixed and subjected to Gram staining, and the smear was placed under an oil immersion lens for observation after being dried. A result of Gram staining was bluish violet, which indicates that the *Lactobacillus gasseri* HMV18 is Gram-positive bacteria, as shown in FIG. 2.

2.2 Catalase Test

Figure 3:
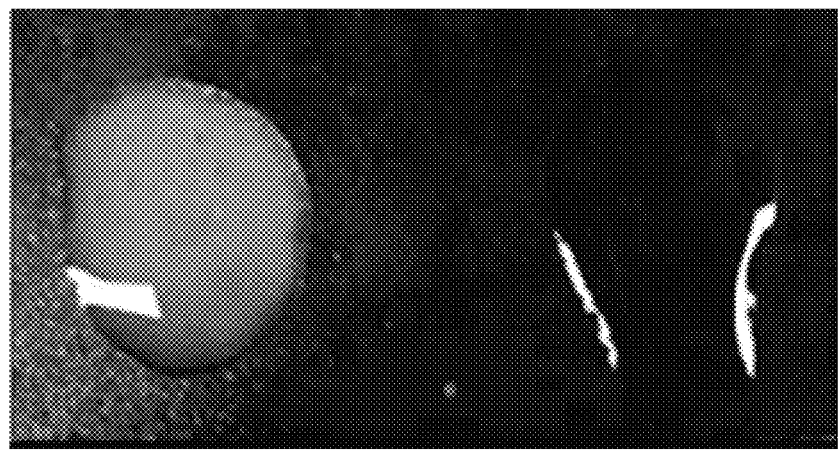
FIG. 3 shows a result of an $H_2O_2$ test of the *Lactobacillus gasseri* HMV18 of the Embodiment 1 of the present disclosure.

A proper amount of the smooth white colony medium solution obtained at 1.3 was picked, and mixed with a 3% $H_2O_2$ solution to obtain a mixed solution. A result of the mixed solution was negative, which indicates that the *Lactobacillus gasseri* HMV18 does not produce $H_2O_2$ enzyme, as shown in FIG. 3.

2.3 Biochemical Identification

The smooth white colony obtained at 1.3 was taken, cultured overnight, and centrifuged to obtained a bacteria precipitate III, the bacteria precipitate III was resuspended with a phosphate buffered saline (PBS) solution to prepare a 0.5 McFarland Standards (MCF) bacteria solution, the 0.5 MCF bacteria solution was respectively inoculated to a medium of a biochemical identification kit for *Lactobacillus*, and 100 µl of the medium in each bottle included: cellobiose, lactose, inulin, raffinose, sucrose, sorbitol, salicin, mannite, maltose, aesculin, 1% sodium hippurate, where a liquid level of the aesculin was covered with sterile paraffin. The culture was completed to obtain a bacteria precipitate IV, and the bacteria precipitate IV was placed on a record card for observation. After the test was finished, 0.2 ml of a ninhydrin solution was added into the bacteria precipitate IV during observation, and a result was read after the bacteria precipitate IV was placed in a water bath or incubator at 36±1° C. for 10 min. The result showed that the *Lactobacillus gasseri* HMV18 may disintegrate the cellobiose, the lactose, the inulin, the raffinose, the sucrose, the salicin, the maltose, as shown in Table 1 illustrated in FIG. 22. Table 1 shows the Biochemical Identification of the *Lactobacillus gasseri* HMV18, where +: positive reaction; −: negative reaction, a: automatic biochemical analysis by VITEK-2 System; b: biochemical analysis by the Hopebio LAB Biochemical Test Kit.

2.4 Genome Extraction and Species Identification by Sequencing 16S rDNA

Genome extraction: the smooth white colony medium solution obtained at 1.3 was taken, cultured overnight, and centrifuged to obtained a thallus, the thallus was crushed by using a paramagnetic particle method, a genome of the thallus was extracted, and a sequence of 16S rDNA was amplified, an polymerase chain reaction (PCR) product was purified to obtain an agarose gel, the agarose gel was subjected to DNA sequencing to obtain the sequence of 16S rDNA, the sequence was compared with that of known bacteria in database to acquire species information of a sample, and a phylogenetic tree was constructed by selecting sequences of approximate bacteria.

A result showed that the new isolate was the *Lactobacillus gasseri*, and had a far genetic relationship with 29 known strains of *Lactobacillus gasseri* in the Genebank.

Figure 4:
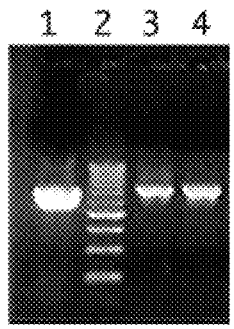
FIG. 4 shows a result of agarose gel eletrophoresis of a PCR amplified product of whole 16S rDNA of the *Lactobacillus gasseri* HMV18 of the Embodiment 1 of the present disclosure.
Figure 5:
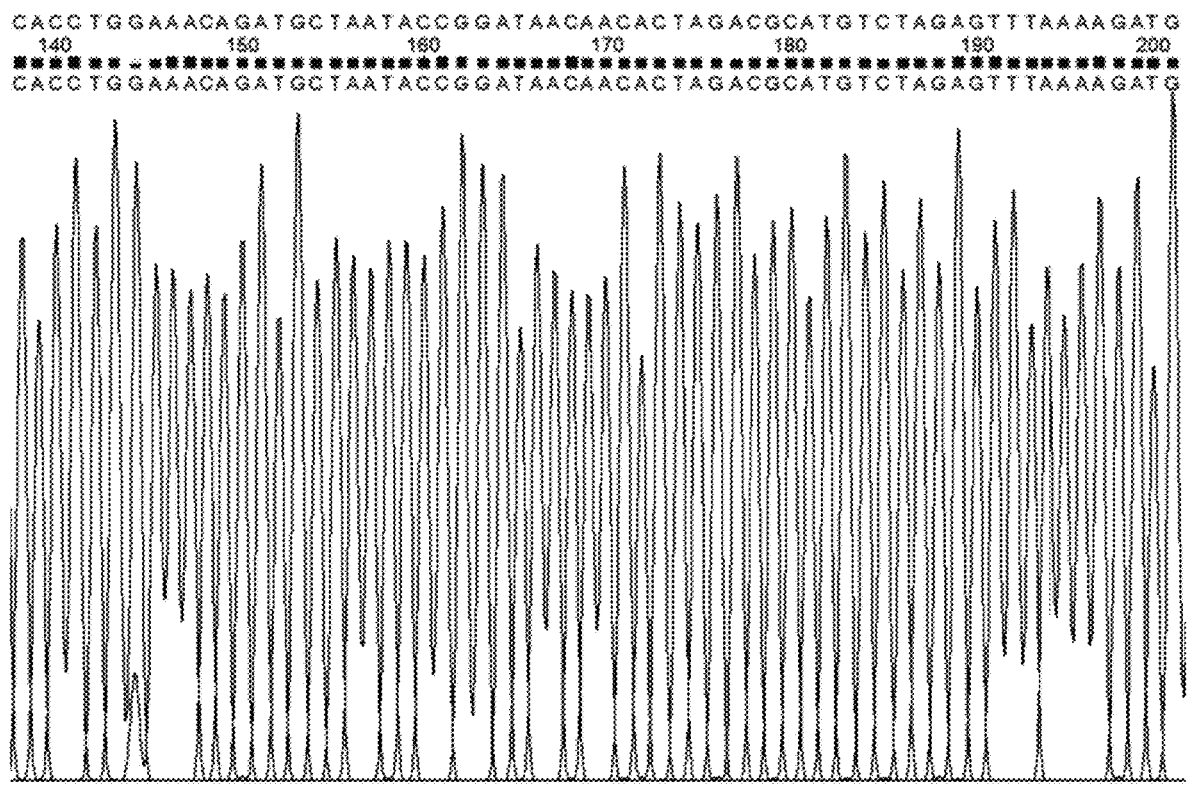
FIG. 5 shows a result of sequencing identification of the PCR amplified product of the *Lactobacillus gasseri* HMV18 of the Embodiment 1 of the present disclosure (the sequence is SEQ ID No. 2)

A result of agarose gel eletrophoresis of the PCR amplified product of the whole 16S rDNA is shown in FIG. 4 (where: Lane 1 is a positive control, a standard strain of *Lactobacillus salivarias* with a number of CGMCC1. 1881; Lane 2 is DNA Marker; Lane 3 is *E. coli* K-12 MG1655; and Lane 4 is the new isolate strains), and a result of sequencing identification of the agarose gel of the PCR amplified product is shown in FIG. 5. Based on the Blast species specificity identification made by the National Center for Biotechnology Information (NCBI) of the United States, it can be determined that the *Lactobacillus gasseri* obtained by the present disclosure is a new strain of *Lactobacillus gasseri*, and is named HMV18.

3. Safety Evaluation of the *Lactobacillus gasseri* HMV18

3.1 Drug-Resistance Test

Figure 6:
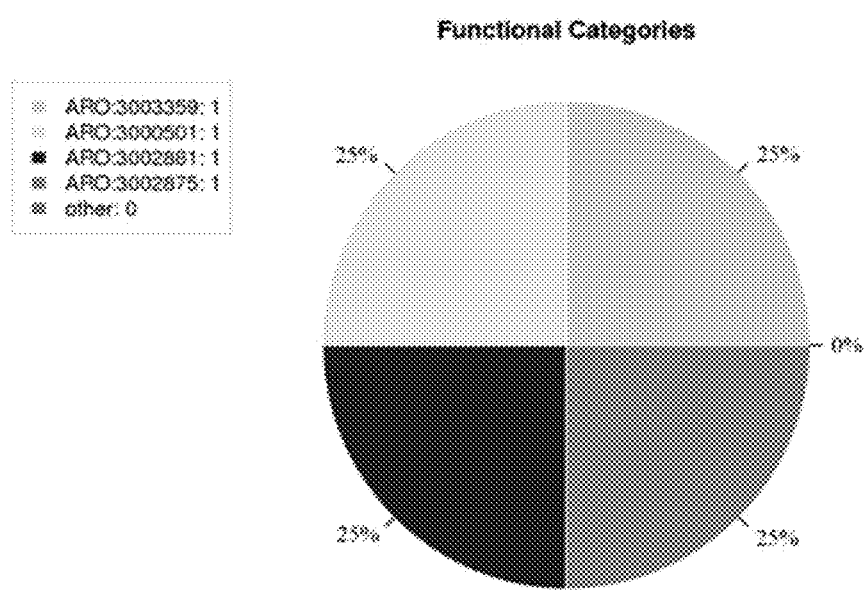
FIG. 6 shows an analysis result of the Comprehensive Antibiotic Research Database (CARD) of the *Lactobacillus gasseri* HMV18 of the Embodiment 1 of the present disclosure.
Figure 7:
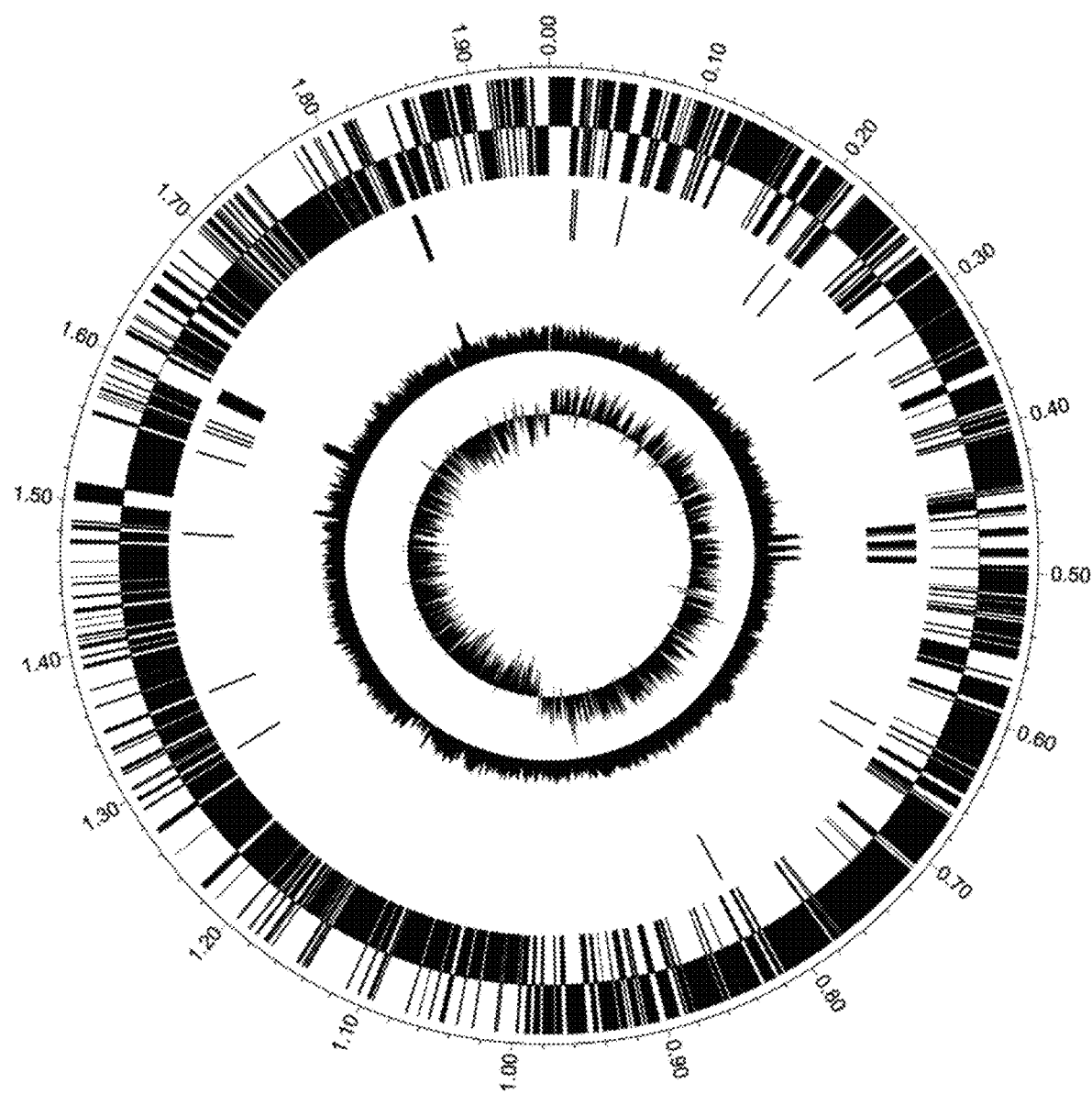
FIG. 7 shows bacteria accomplishment diagram of the *Lactobacillus gasseri* HMV18 of the Embodiment 1 of the present disclosure.

The *Lactobacillus gasseri* HMV18 was subjected to whole genome sequencing, and a result showed that its genome included chromosomes of 1.95 megabase pair (Mb), small plasmids of 4626 base pair (Bp), large plasmids of 3.2 kilobase pair (Kb) and bacteriophage of 3.9 Kb. Based on analysis of the Comprehensive Antibiotic Research Database (CARD), a gene predicting result showed that mycoplasm of the *Lactobacillus gasseri* HMV18 only carried suspicious sequences resisting rifampicin, streptomycin, lincoamides antibiotics and alphamycin suspicious sequence, there is no antibiotic resistance gene on the plasmid or bacteriophage, which indicates that the *Lactobacillus gasseri* HMV18 has no threat of horizontal transfer of drug-resistance (as shown in FIG. 6). A bacteria accomplishment diagram of the *Lactobacillus gasseri* HMV18 (as shown in FIG. 7).

3.2 Hemolysis Test

Figure 8:
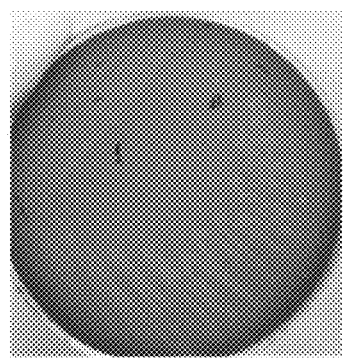
FIG. 8 shows hemolysis of the *Lactobacillus gasseri* HMV18 of the Embodiment 1 of the present disclosure.

A hemolytic property of the *Lactobacillus gasseri* HMV18 was evaluated by using a blood agar plate inoculation method, a test result showed that a grass green ring of 1-2 mm appeared in the medium around the colony of the *Lactobacillus gasseri* HMV18, red blood cells in its a hemolysis ring were not completely dissolved (as shown in FIG. 8). It is indicated that the *Lactobacillus gasseri* HMV18 is non-pathogenic or conditioned pathogenic bacteria.

3.3 Animal Test 3.3.1 Healthy adult male Kunming mice of 18-22 g were randomly divided into a control group and a test group for the animal test. The environmental temperature was set to be 22° C., the humidity was set to be 60%, and the illumination was set to be 12 h, mouse food and purified water were given sufficiently every day, and the mice were subjected to the test after being fed for 3 days. A grouping situation is shown in Table 2.

Preparation of a bacteria suspension of the *Lactobacillus gasseri* HMV18: bacteria of activated *Lactobacillus gasseri* HMV18 were placed into a 15 mL centrifuge tube to obtain a bacteria suspension of the *Lactobacillus gasseri* HMV18, and the bacteria suspension of the *Lactobacillus gasseri* HMV18 was cultured in an incubator for 18-24 h. The bacteria suspension of the *Lactobacillus gasseri* HMV18 subjected to culture in the incubator was added into an MRS liquid medium and an optical density (OD) value was measured, the OD value was regulated by repeatedly diluting the bacteria suspension of the *Lactobacillus gasseri* HMV18 with an MRS liquid until a spectro-photometer showed 1 OD, and the obtained the bacteria suspension of the *Lactobacillus gasseri* HMV18 may be used for the animal test.

Figure 9:
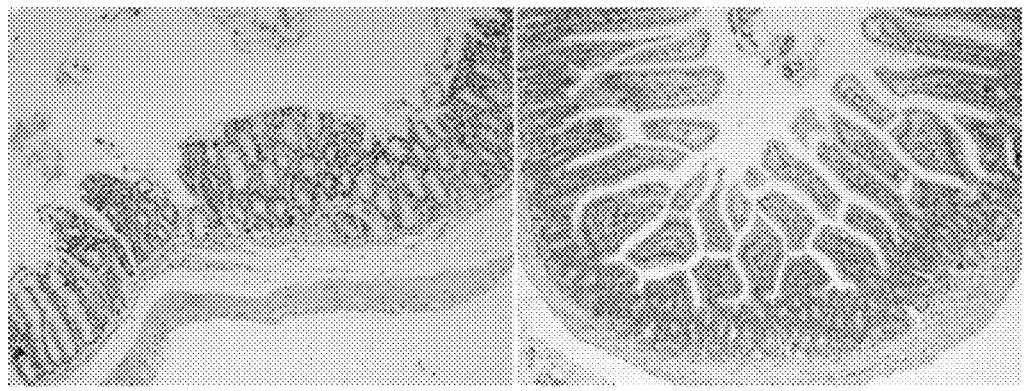
FIG. 9 shows a gastric mucosa section in a gavage test of the *Lactobacillus gasseri* HMV18 of the Embodiment 1 of the present disclosure.

Respectively, a damage of the *Lactobacillus gasseri* HMV18 to gastric mucosa of the mouse was detected by a gavage test, whether the *Lactobacillus gasseri* HMV18 causes peritonitis was detected by an intraperitoneal injection test, whether the *Lactobacillus gasseri* HMV18 causes infection was detected by a subcutaneous inoculation test, and whether the *Lactobacillus gasseri* HMV18 causes bacteremia and septicemia was detected by an intravenous injection test. Results are shown in Table 3. A gastric mucosa section is shown in FIG. 9.

TABLE 2

Grouping of an animal test

| Test way | Number | Administration way | Investigated items |
|---|---|---|---|
| Gavage test | 5 | Gavage of HMV18 for 7 days | Weight, daily intake, viscera index, section, blood routine, and blood biochemistry |
| | 5 | Gavage of PBS for 7 days | |
| Intraperitoneal injection test | 5 | Intraperitoneal injection of HMV18 for 2 days | Weight, daily intake, viscera index, section, bacterial translocation test, blood routine, and blood biochemistry |
| | 5 | Intraperitoneal injection of PBS for 2 days | |
| | 5 | Intraperitoneal injection of HMV18 for 4 days | |
| | 5 | Intraperitoneal injection of PBS for 4 days | |
| | 5 | Intraperitoneal injection of HMV18 for 8 days | |
| | 5 | Intraperitoneal injection of PBS for 8 days | |
| Subcutaneous inoculation test | 5 | Subcutaneous injection of HMV18 for 2 days | Weight, daily intake, viscera index, section, skin section, blood routine, and blood biochemistry |
| | 5 | Subcutaneous injection of PBS for 2 days | |

TABLE 3

Results of various investigated items of a gavage test

| | | | Days (d) | | | | | | | |
|---|---|---|---|---|---|---|---|---|---|---|
| | | | 1 | 2 | 3 | 4 | 5 | 6 | 7 | 8 |
| Gavage of HMV18 for 7 days | Weight (g) | | $33.60 \pm 2.35^a$ | $34.43 \pm 1.83^a$ | $34.60 \pm 1.91^a$ | $34.13 \pm 2.00^a$ | $35.67 \pm 1.97^a$ | $35.59 \pm 1.94^a$ | $36.07 \pm 1.83^a$ | $35.06 \pm 1.90^a$ |
| | Daily intake (g/mouse) | | 5.32 | 5.56 | 5.44 | 6.21 | 5.96 | 6.76 | 5.93 | 6.19 |
| | Weight of viscera (g) | Heart | | | | $4.85 \pm 0.43^b$ | | | | |
| | | Liver | | | | $45.90 \pm 6.12^a$ | | | | |
| | | Spleen | | | | $3.68 \pm 1.32^a$ | | | | |
| | | Lung | | | | $5.79 \pm 0.60^a$ | | | | |
| | | Kidney | | | | $16.12 \pm 2.40^a$ | | | | |
| Gavage of PBS for 7 days | Weight (g) | | $32.55 \pm 2.25^a$ | $33.50 \pm 2.60^a$ | $33.60 \pm 2.20^a$ | $34.05 \pm 2.15^a$ | $38.90 \pm 1.20^a$ | $34.99 \pm 0.46^a$ | $35.03 \pm 1.04^a$ | $34.43 \pm 0.82^a$ |
| | Daily intake (g/mouse) | | 4.65 | 4.23 | 4.45 | 5.51 | 5.32 | 5.28 | 5.80 | 5.7 |
| | Weight of viscera (g) | Heart | | | | $4.26 \pm 1.65^b$ | | | | |
| | | Liver | | | | $42.68 \pm 1.68^a$ | | | | |
| | | Spleen | | | | $3.40 \pm 1.05^a$ | | | | |
| | | Lung | | | | $5.33 \pm 0.89^a$ | | | | |
| | | Kidney | | | | $18.97 \pm 1.73^a$ | | | | |

Notes:

lowercase letters for shoulder labels in the same column indicate that there is no significant difference (p-value (P) > 0.05).

TABLE 4

Investigation results of an intraperitoneal injection test (2 days)

|  |  | Days (d) | | |
|---|---|---|---|---|
|  |  | 1 | 2 | 3 |
| Intraperitoneal injection of HMV18 for 2 days | Weight (g) | 37.51 ± 5.82$^a$ | 37.34 ± 6.08$^a$ | 34.20 ± 1.60$^a$ |
|  | Daily intake (g/mouse) | 6.75 | 7.14 | / |
|  | Weight of viscera (g) Heart |  | 5.14 ± 0.90$^a$ |  |
|  | Liver |  | 49.05 ± 7.38$^a$ |  |
|  | Spleen |  | 6.43 ± 4.72$^a$ |  |
|  | Lung |  | 5.81 ± 1.02$^a$ |  |
|  | Kidney |  | 14.75 ± 3.14$^a$ |  |
| Intraperitoneal injection of PBS for 2 days | Weight (g) | 34.87 ± 1.33$^a$ | 35.83 ± 1.43$^a$ | 37.71 ± 5.55$^a$ |
|  | Daily intake (g/mouse) | 5.79 | 5.55 | / |
|  | Weight of viscera (g) Heart |  | 6.06 ± 0.65$^a$ |  |
|  | Liver |  | 42.1 ± 2.06$^a$ |  |
|  | Spleen |  | 7.75 ± 3.13$^a$ |  |
|  | Lung |  | 6.06 ± 0.41$^a$ |  |
|  | Kidney |  | 16.72 ± 1.18$^a$ |  |

Notes:
lowercase letters for shoulder labels in the same column indicate that there is no significant difference (P > 0.05).

TABLE 5

Investigation results of an intraperitoneal injection test (4 days)

|  |  | Days (d) | | | | |
|---|---|---|---|---|---|---|
|  |  | 1 | 2 | 3 | 4 | 5 |
| Intraperitoneal injection of HMV18 for 4 days | Weight (g) | 30.90 ± 1.63$^a$ | 32.67 ± 1.54$^a$ | 33.13 ± 1.40$^a$ | 34.00 ± 1.96$^a$ | 37.80 ± 1.17$^a$ |
|  | Daily intake (g/mouse) | 5.60 | 6.54 | 6.48 | 6.50 | / |
|  | Weight of viscera (g) Heart |  |  | 5.17 ± 0.32$^a$ |  |  |
|  | Liver |  |  | 46.35 ± 3.53$^a$ |  |  |
|  | Spleen |  |  | 3.88 ± 0.49$^a$ |  |  |
|  | Lung |  |  | 6.27 ± 0.63$^a$ |  |  |
|  | Kidney |  |  | 15.53 ± 1.78$^a$ |  |  |
| Intraperitoneal injection of PBS for 4 days | Weight (g) | 37.20 ± 1.59$^a$ | 37.97 ± 1.64$^a$ | 38.57 ± 1.41$^a$ | 38.37 ± 1.61$^a$ | 33.58 ± 1.55$^a$ |
|  | Daily intake (g/mouse) | 4.44 | 7.12 | 5.84 | 6.00 | / |
|  | Weight of viscera (g) Heart |  |  | 5.81 ± 0.38$^a$ |  |  |
|  | Liver |  |  | 42.49 ± 1.40$^a$ |  |  |
|  | Spleen |  |  | 2.83 ± 0.21$^a$ |  |  |
|  | Lung |  |  | 5.83 ± 0.79$^a$ |  |  |
|  | Kidney |  |  | 16.43 ± 2.04$^a$ |  |  |

Notes:
lowercase letters for shoulder labels in the same column indicate that there is no significant difference (P > 0.05).

TABLE 6

Investigation results of an intraperitoneal injection test (8 days)

|  |  | Days (d) | | | | | | | | |
|---|---|---|---|---|---|---|---|---|---|---|
|  |  | 1 | 2 | 3 | 4 | 5 | 6 | 7 | 8 | 9 |
| Intraperitoneal injection of HMV18 for 8 days | Weight (g) | 33.17 ± 0.84$^a$ | 32.77 ± 1.54$^a$ | 34.10 ± 2.41$^a$ | 34.33 ± 2.08$^a$ | 33.13 ± 2.43$^a$ | 35.50 ± 0.46$^a$ | 35.03 ± 1.04$^a$ | 34.43 ± 0.82$^a$ | 34.42 ± 1.19$^a$ |
|  | Daily intake (g/mouse) | 3.41 | 4.88 | 5.33 | 5.20 | 7.59 | 5.59 | 6.21 | 6.36 | / |
|  | Weight of viscera (g) Heart |  |  |  |  | 6.14 ± 0.39$^a$ |  |  |  |  |
|  | Liver |  |  |  |  | 45.40 ± 1.73$^a$ |  |  |  |  |
|  | Spleen |  |  |  |  | 3.47 ± 0.37$^a$ |  |  |  |  |
|  | Lung |  |  |  |  | 5.82 ± 0.22$^a$ |  |  |  |  |
|  | Kidney |  |  |  |  | 14.87 ± 1.17$^a$ |  |  |  |  |
| PBS intraperitoneal injection for 8 days | Weight (g) | 31.62 ± 0.40$^a$ | 32.87 ± 0.46$^a$ | 33.10 ± 0.57$^a$ | 33.77 ± 0.33$^a$ | 33.77 ± 0.92$^a$ | 34.99 ± 0.46$^a$ | 35.03 ± 1.04$^a$ | 34.43 ± 0.82$^a$ | 34.42 ± 1.19$^a$ |
|  | Daily intake (g/mouse) | 6.61 | 5.48 | 5.92 | 4.85 | 7.41 | 5.02 | 4.47 | 4.99 | / |
|  | Weight of viscera (g) Heart |  |  |  |  | 4.76 ± 0.43$^a$ |  |  |  |  |
|  | Liver |  |  |  |  | 46.70 ± 3.47$^a$ |  |  |  |  |
|  | Spleen |  |  |  |  | 5.04 ± 0.25$^a$ |  |  |  |  |
|  | Lung |  |  |  |  | 5.34 ± 0.26$^a$ |  |  |  |  |
|  | Kidney |  |  |  |  | 15.94 ± 3.02$^a$ |  |  |  |  |

Notes:
lowercase letters for shoulder labels in the same column indicate that there is no significant difference (P > 0.05).

TABLE 7

Results of a bacteria translocation test of an intraperitoneal injection test

| Group | Colony | Ascites | Liver |
|---|---|---|---|
| Intraperitoneal injection of HMV18 for 2 days | Large colony, smooth, white | 1/3 | 0/3 |
| | Medium colony, unsmooth, relatively transparent | 0/3 | 0/3 |
| | Small colony, smooth, white | 2/3 | 1/3 |
| Intraperitoneal injection of PBS for 2 days | Large colony, smooth, white | 0/3 | 0/3 |
| | Medium colony, unsmooth, relatively transparent | 0/3 | 1/3 |
| | Small colony, smooth, white | 0/3 | 0/3 |
| HMV18 intraperitoneal injection for 4 days | Large colony, smooth, white | 2/3 | 1/3 |
| | Medium colony, unsmooth, relatively transparent | 0/3 | 1/3 |
| | Small colony, smooth, white | 0/3 | 1/3 |
| PBS intraperitoneal injection for 4 days | Large colony, smooth, white | 0/3 | 0/3 |
| | Medium colony, unsmooth, relatively transparent | 0/3 | 0/3 |
| | Small colony, smooth, white | 0/3 | 0/3 |
| Intraperitoneal injection of HMV18 for 8 days | Large colony, smooth, white | 0/3 | 0/3 |
| | Medium colony, unsmooth, relatively transparent | 0/3 | 3/3 |
| | Small colony, smooth, white | 0/3 | 0/3 |
| Intraperitoneal injection of PBS for 8 days | Large colony, smooth, white | 0/3 | 0/3 |
| | Medium colony, unsmooth, relatively transparent | 0/3 | 1/3 |
| | Small colony, smooth, white | 0/3 | 0/3 |

Figure 10:
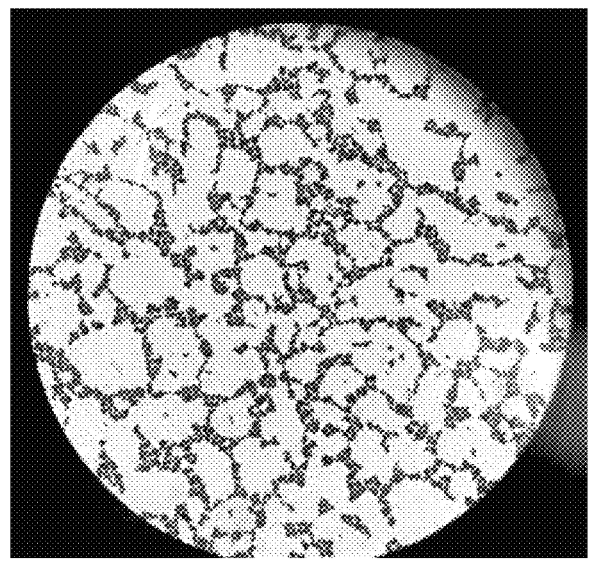
FIG. 10 shows large colony morphology in an intraperitoneal injection test of the *Lactobacillus gasseri* HMV18 of the Embodiment 1 of the present disclosure.
Figure 11:
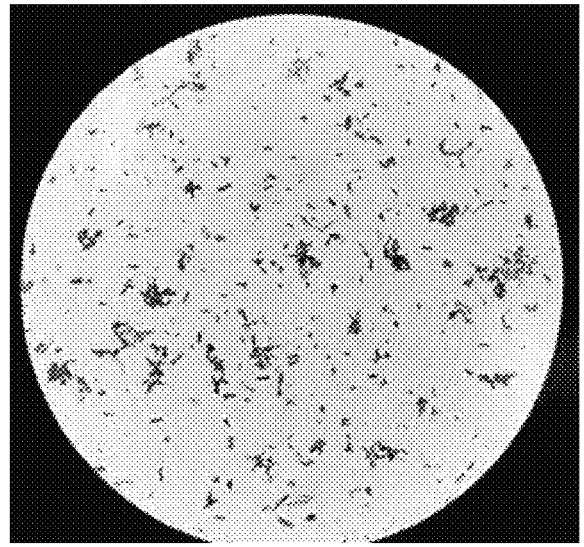
FIG. 11 shows medium colony morphology in the intraperitoneal injection test of the *Lactobacillus gasseri* HMV18 of the Embodiment 1 of the present disclosure.
Figure 12:
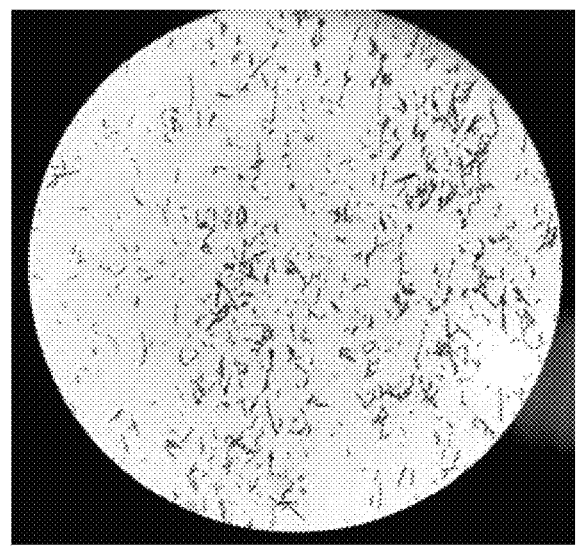
FIG. 12 shows small colony morphology in the intraperitoneal injection test of the *Lactobacillus gasseri* HMV18 of the Embodiment 1 of the present disclosure.

Large colony morphology of each group is shown in FIG. 10, medium colony morphology of each group is shown in FIG. 11, and small colony morphology of each group is shown in FIG. 12.

TABLE 8

Investigation results of a subcutaneous injection test

| Weight (g) | | 23.74 ± 0.71 | 24.52 ± 0.34 | 24.98 ± 0.45 |
|---|---|---|---|---|
| Daily intake (g/mouse) | | 4.99 | 6.60 | 5.23 |
| Weight of viscera (g) | Heart | | 4.81 ± 0.09$^a$ | |
| | Liver | | 57.50 ± 6.50$^a$ | |
| | Spleen | | 4.54 ± 0.66$^a$ | |
| | Lung | | 7.34 ± 0.65$^a$ | |
| | Kidney | | 13.89 ± 1.27$^a$ | |

Notes:
lowercase letters for shoulder labels in the same column indicate that there is no significant difference (P > 0.05).

Figure 13:
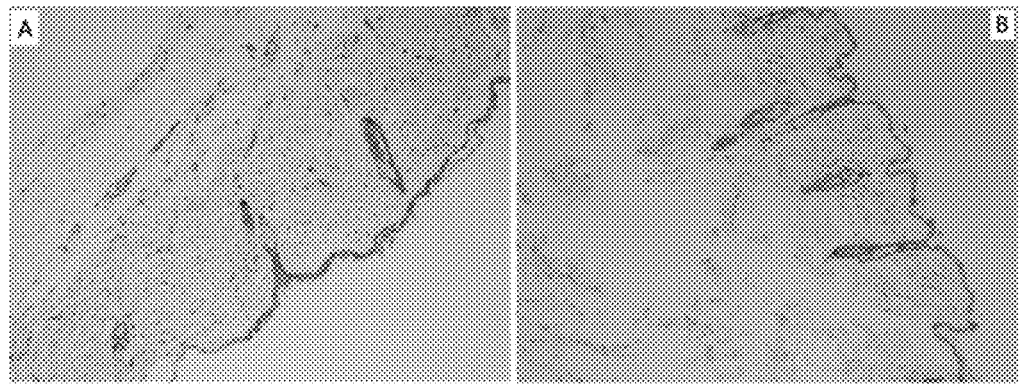
FIG. 13 shows a skin section in a subcutaneous injection test of the *Lactobacillus gasseri* HMV18 of the Embodiment 1 of the present disclosure.

The skin section is shown in FIG. 13, where diagram A is a skin subjected to subcutaneous injection of the *Lactobacillus gasseri* HMV18, diagram B is a skin subjected to subcutaneous injection of phosphate buffered saline (PBS).

3.4 Detection of Harmful Metabolites

Amino acid decarboxylase media respectively including histidine, lysine, ornithine, tyrosine and arginine, and an amino acid control MRS medium were prepared. Detection tubes were obtained after the *Lactobacillus gasseri* HMV18 was inoculated to the amino acid decarboxylase media, a control tube was obtained after the *Lactobacillus gasseri* HMV18 was inoculated to the amino acid control MRS medium, and the detection tubes and the control tube were subjected to a decarboxylase test respectively. The control tube should be yellow, if the detection tube was purple (an indicator was bromocresol purple), it was positive, and if the detection tube was yellow, it was negative. Excessive biogenic amine would cause human poisoning, lead to serious consequences and develop severe reactions such as headache, a blood pressure change, a breathing disorder, palpitation and vomiting. Results of the *Lactobacillus gasseri* HMV18 are shown in Table 9, the *Lactobacillus gasseri* HMV18 did not produce decarboxylase, and did not disintegrate amino acids nor decarboxylate them so as to avoid production of the harmful biogenic amine.

TABLE 9

Results of a decarboxylase test

| Amino acid | Histidine | Lysine | Ornithine | Tyrosine | Arginine | MRS medium |
|---|---|---|---|---|---|---|
| Result | Yellow | Yellow | Yellow | Yellow | Yellow | Yellow |

3.5 Mucin Degradation Test

The smooth white colony medium solution obtained at 1.3 was taken and cultured overnight, 1% of the cultured smooth white colony medium solution was inoculated to 4 types of MRS media (each 100 ml of the medium was added with mucin and/or glucose according to an additive amount shown in Table 10), and the MRS media were cultured for incubation at 37° C. for 48 h. After incubation, growth of bacteria in the 4 types of MRS media was evaluated by measuring absorbance at 600 nm and 12 h, 24 h, 36 h and 48 h. Mucin is a main component of epithelial tissue, covers a surface of mucosa, and plays protection and lubrication actions on epithelial tissue. When bacteria may use and degrade mucin, it indicates that they may perform bacteria translocation through organism barrier. When safety of microorganism is detected, a dissolving capacity of mucus should be detected to determine translocation ability of bacteria. Results are shown in Table 10, which indicated that *Lactobacillus gasseri* HMV18 might not degrade and use mucin, and did not have the bacteria translocation ability in vivo, the results were consistent with the results of the safety evaluation of the *Lactobacillus gasseri* HMV18 subcutaneously inoculated into mice, a skin of the inoculated part did not have inflammatory response, and the *Lactobacillus gasseri* HMV18 did not spread in subcutaneous tissue.

TABLE 10

Results of a mucin degradation test (OD value)

| Additive and additive amount | 0 h | 12 h | 24 h | 36 h | 48 h | 72 h |
|---|---|---|---|---|---|---|
| 0.25 g of mucin | 0.019 | 0.229 | 0.287 | 0.248 | 0.288 | 0.161 |
| 0.5 g of mucin | 0 | 0.03 | 0.052 | 0.036 | 0.048 | 0.006 |
| 0.2 g of glucose | 0 | 1.999 | 1.627 | 1.586 | 1.598 | 1.36 |
| 0.2 g of glucose + 0.25 g of mucin | 0 | 0.518 | 0.392 | 0.317 | 0.512 | 0.132 |

4. Result Analysis of Whole Genome Sequencing

The results of whole genome sequencing showed that, its chromosomes carry gatAX genes (see Table 11), which indicates that the *Lactobacillus gasseri* HMV18 may produce bacteriocin Gassericin T, which has an antagonistic effect on vaginal pathogenic bacteria.

TABLE 11

Gene predicting results of whole genome sequencing of the *Lactobacillus gasseri* HMV18

| Number of sequenced gene | Number of gene\| number of protein in the Genebank | Number of amino acid residues (similarity) | Gene name |
|---|---|---|---|
| 0558 | gi\|896139926\|ref\|WP_049159833.1\| | 75/75(100.00) | gatA |
| 0559 | gi\|489745186\|ref\|WP_003649213.1\| | 65/65(100.00) | gatX |

Embodiment 2

The embodiment provides a secreted protein of the *Lactobacillus gasseri*, and its preparation method includes:

1. Separation of the Secreted Protein of the *Lactobacillus gasseri*

The *Lactobacillus gasseri* HMV18 cryopreserved at −80° C. was taken and inoculated to 10 ml of an improved MRS liquid medium according to an inoculation amount of 5 weight percent (wt %), and the inoculated improved MRS liquid medium was uniformly mixed and cultured in a thermostatic incubator at 37° C. for 20 h under an anaerobic condition. The activization succeeded if the medium was opacity, and a first-generation bacteria solution was obtained.

The first-generation bacterial solution was taken and inoculated to an improved MRS liquid medium in a sealed glass bottle with a screw mouth according to an inoculation amount of 3 wt %, and the inoculated improved MRS liquid medium was cultured in a thermostatic incubator at 37° C. for 24 h under an anaerobic condition to obtain a second-generation bacterial solution.

The second-generation bacterial solution was poured into a 50 ml centrifuge tube and centrifuged at 5,000 rpm for 10 min after being balanced, and a precipitate was removed to obtain a supernate I;

1 mol/L NaOH and 1 mol/L catalase were added into the supernate I to obtain a mixture III and regulate a pH value of the mixture III to be 6.2, and the mixture III was stirred at 4° C. for 2 h, allowed to stand for 2 h, centrifuged at 4° C. at 12,000 rpm for 30 min, and its precipitate was removed to obtain a supernate II;

a finely ground ammonium sulfate powder was slowly added into the supernate II by means of a weighing spoon to obtain a mixture IV, the mixture IV was stirred at 4° C. for 2 h by means of a magnetic stirrer, allowed to stand for 10 h, and centrifuged at 4° C. at 12,000 rpm for 30 min, a supernate was removed to obtain a precipitate, namely a crude product of the secreted protein of the *Lactobacillus gasseri*.

2. Purification of the Secreted Protein of the *Lactobacillus gasseri*

A dialysis bag was boiled in 2% $NaHCO_3$·1 millimolar molar per litre (mM) ethylenediaminetetraacetic acid (EDTA) (PH 8.0) for 10 min, thoroughly washed with double distilled water, boiled in 1 mM EDTA for 10 min, cooled, and thoroughly washed with a dialysis solution. The crude product of the secreted protein of the *Lactobacillus gasseri* obtained at step 1 was transferred into the dialysis bag by means of a pipette, the dialysis bag was sealed, and immersed into a PBS-0.2 g sodium azide dialysis solution, a magnetic stirrer was used for stirring at 4° C., the PBS-0.2 g sodium azide dialysis solution was replaced every 6 hours for totally two times, and the dialysis solution was replaced with a PBS dialysis solution without sodium azide at a third time. After dialysis for 24 h, a product was collected, namely the purified secreted protein of the *Lactobacillus gasseri*.

3. Identification of the Secreted Protein of the *Lactobacillus gasseri*

Figure 14:
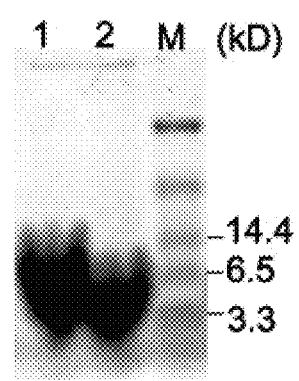
FIG. 14 shows a result of Coomassie blue staining of a secreted protein of the *Lactobacillus gasseri* of Embodiment 2 of the present disclosure subjected to SDS-PAGE.

The secreted protein of the *Lactobacillus gasseri* obtained at step 2 was subjected to sodium dodecyl sulfate polyacrylamide gel electrophoresis (SDS-PAGE) and Coomassie blue staining (as shown in FIG. 14, where 1 is a precipitated protein obtained when an additive amount of ammonium sulfate is 30 wt %, 2 is a precipitated protein obtained when an additive amount of ammonium sulfate is 40 wt %, and M is Marker), and a comparison identification of molecular weights was carried out. Results indicated that the secreted protein of the *Lactobacillus gasseri* coded and expressed bacteriocin Gassericin T (Gat A and Gat X).

Embodiment 3

The embodiment of the present disclosure provides an effect of an antibacterial test of the secreted protein of the *Lactobacillus gasseri* obtained in the Embodiment 2.

Figure 15:
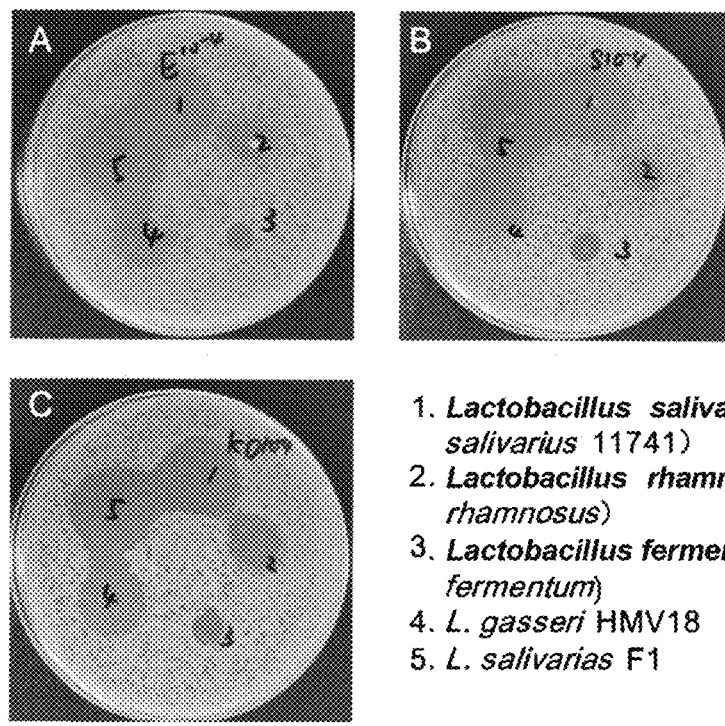
FIG. 15 shows a result of an anti-*Escherichia coli* test of a secreted protein of the *Lactobacillus gasseri* of Embodiment 3 of the present disclosure.

Antibacterial activities of the secreted protein of the *Lactobacillus gasseri* obtained in the Embodiment 2 to *Escherichia coli* (*E. Coli*), *Klebsiella oxytoca* (*K. oxytaca*) and *Staphylococcus aureus* (*S. aureus*) were detected by using an Oxford cup method. *Escherichia coli* (*E. Coli*), *Klebsiella oxytoca* (*K. oxytaca*) and *Staphylococcus aureus* (*S. aureus*) were respectively inoculated to LB plate media by using a streak inoculation method, the inoculated LB plate media were cultured at 37° C. for 18 h, and *Escherichia coli* (*E. Coli*), *Klebsiella oxytoca* (*K. oxytaca*) and *Staphylococcus aureus* (*S. aureus*) were respectively resuscitated to obtain single colonies. The single colonies were picked and inoculated to an LB liquid medium, the inoculated LB liquid medium was cultured at 37° C. for 24 h, and centrifuged at 5,000 r/min for 10 min to obtain a bacteria precipitate V. The bacteria precipitate V was diluted with normal saline to $1×10^9$ CFU/mL to obtain a bacteria precipitate VI, where at this time a spectro-photometer read that $OD_{600}=1$, and then the bacteria precipitate VI was diluted with normal saline to prepare a bacteria suspension II at a concentration of 105 CFU/mL. 0.1 mL of the bacteria suspension II was sucked up, and uniformly coated onto an LB solid medium by using sterile glass beads. Oxford cups were uniformly placed on the LB solid medium coated with the bacteria suspension II, the neutralized secreted protein of the *Lactobacillus gasseri* obtained in the Embodiment 2 was respectively added into the Oxford cups, and incubated at 37° C. for 24 h. Results showed that a diameter of an inhibition zone of the secreted protein of the *Lactobacillus gasseri* secreted by the HMV18 to *Escherichia coli* (*E. coli*) was 15 mm, and an inhibition result was positive, a diameter of an inhibition zone to *Klebsiella oxytoca* (*K. oxytaca*) was 18 mm, and an inhibition result was positive, and a diameter of an inhibition zone to *Staphylococcus aureus* (*S. aureus*) was 17 mm, and an inhibition result was positive (as shown in FIG. 15, where A is the inhibition result for *Escherichia coli*, B is the inhibition result for *Staphylococcus aureus*, and C is the inhibition result for *Klebsiella oxytoca*). 11741 which is a standard stain of *Lactobacillus salivarius* (*L. salivarius*), and *L. salivarius* F1 which is a strain separated from a commercially available probiotics product, were both used as positive control bacteria. The above results showed that the secreted protein of the *Lactobacillus gasseri* secreted by the HMV18 had good inhibition effects on *Escherichia coli*, *Klebsiella oxytoca* and *Staphylococcus aureus*.

Embodiment 4

The embodiment of the present disclosure provides a result of an anti-tumor test of the secreted protein of the *Lactobacillus gasseri* obtained in the Embodiment 2.

Figure 16:
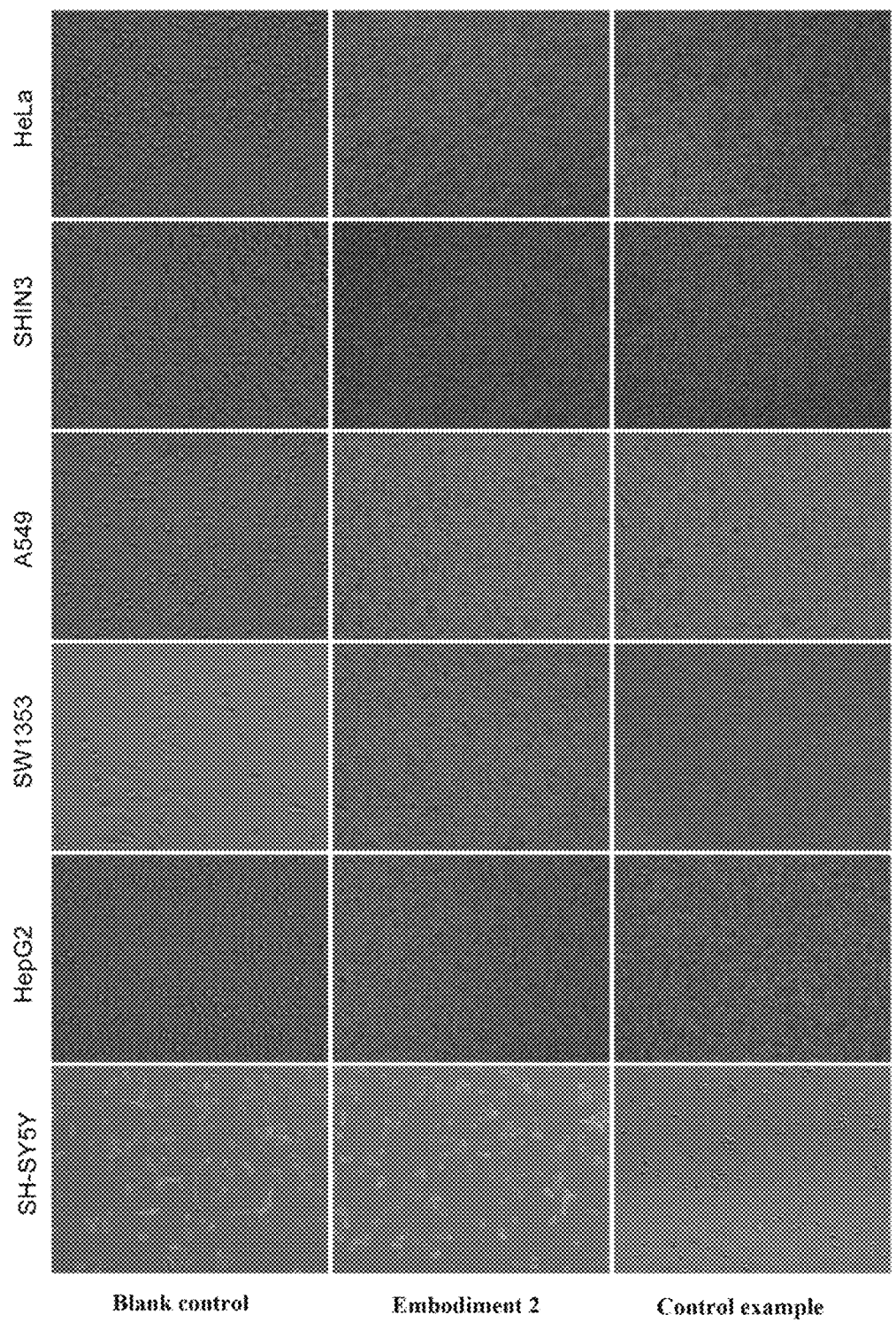
FIG. 16 shows a result of an anti-tumor test of a secreted protein of the *Lactobacillus gasseri* of Embodiment 4 of the present disclosure.

The anaerobic culture in the Embodiment 2 was replaced with an aerobic culture, and a protein was prepared by the separation and purification method in the Embodiment 2, and used as a control example. An improved MRS liquid medium was taken as a blank control, the secreted protein of the *Lactobacillus gasseri* obtained in the Embodiment 2 and the protein obtained in the control example, which were in the same additive amount, were respectively incubated together with cells of a human cervical cancer cell line (Hela cells), a human ovary carcinoma cell line (SHIN3 cells), a human lung adenocarcinoma cell line (A549), a human chondrosarcoma cell line (SW1353 cells), a human hepatocarcinoma cell line (HepG2) and human bone marrow neuroblastoma cell line (SH-SY5Y cells) at 37° C. for 40 min, results are shown in FIG. 16, bulges of the tumor cells incubated together with the secreted protein of the *Lactobacillus gasseri* obtained in the Embodiment 2 gradually shrank and disappeared, and the tumor cells turned round, more than 95% of adherent cells suspended, cytolysis and division may be found after 2 h, a small number of sporadic and relatively complete contours may still be found, but these residual contours were significantly different from a normal cell in terms of size and morphology, and in addition, an oncolytic effect of the secreted protein of the *Lactobacillus gasseri* obtained in the Embodiment 2 was obviously better than that of the protein obtained in the control example. It may be seen from the results that, the secreted protein of the *Lactobacillus gasseri* obtained in the Embodiment 2 did not have obvious selectivity in the oncolysis of the tumor cells, and had good anti-tumor effects on multiple tumors.

Various cells were restored to a normal culture condition for 24 h, adherence was not found again, and finally the cells disrupted and died.

Figure 17:
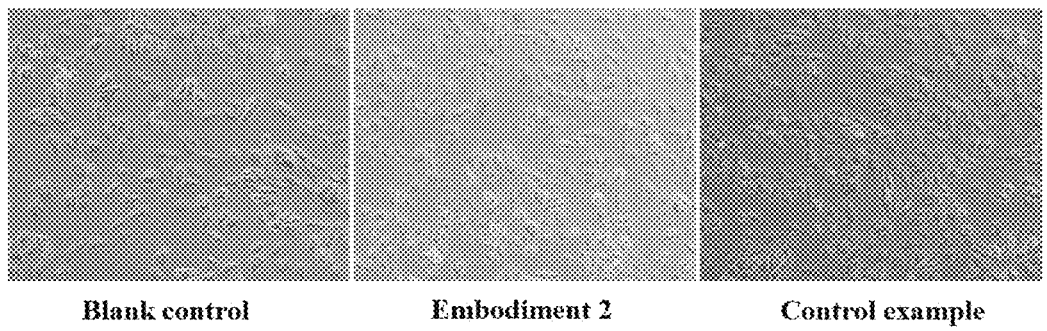
FIG. 17 shows a result of the secreted protein of the *Lactobacillus gasseri* of the Embodiment 4 of the present disclosure in effecting myocardial cells.

Meanwhile, the secreted protein of the *Lactobacillus gasseri* obtained in the Embodiment 2 had no significant effect on a normal myocardial cell line (as shown in FIG. 17).

Figure 18:
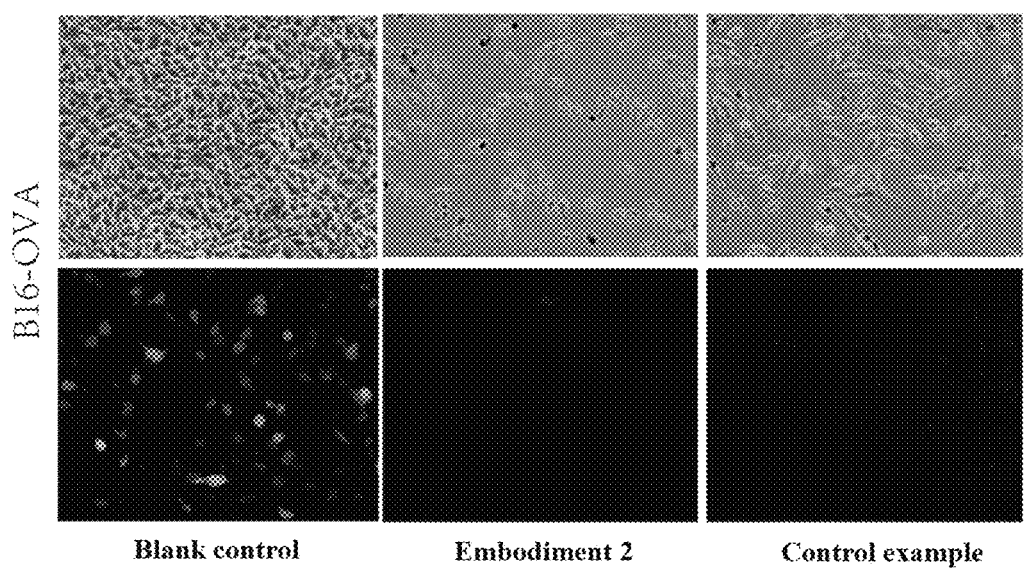
FIG. 18 shows a result of the secreted protein of the *Lactobacillus gasseri* of the Embodiment 4 of the present disclosure in acting on B16-OVA cells.

An improved MRS liquid medium was taken as a blank control, the secreted protein of the *Lactobacillus gasseri* obtained in the Embodiment 2 and the protein of the control example were incubated together with B16-OVA (a melanoma cell line) for 2 h, and cell morphology and expressions of an OVA protein were observed under a microscope. Results showed that the B16-OVA cells in the improved MRS liquid medium still had a small number of expressions of a green fluorescent protein (GFP) compared to normal cultured cells; after being incubated together with the secreted protein of the *Lactobacillus gasseri* obtained in the Embodiment 2, more than 95% of the tumor cells turned round, shed, and suspended, did not have the expressions of the green fluorescent protein, and had a significant GFP oncolytic effect; after being incubated together with the protein of the control example, the B16-OVA cells did not have the expressions of the green fluorescent protein, had fair cell morphology, and did not suspend and shed (as shown in FIG. 18).

Figure 19:
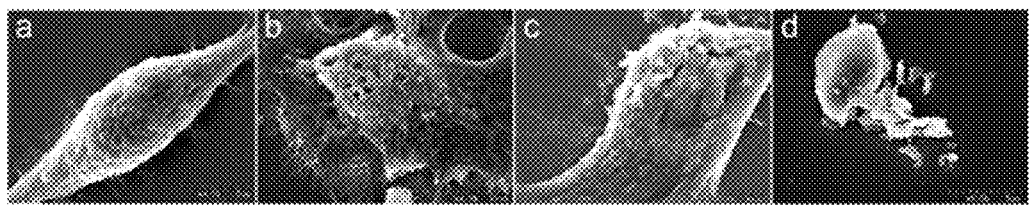
FIG. 19 shows results of the secreted protein of the *Lactobacillus gasseri* of the Embodiment 4 of the present disclosure in acting on a human lung adenocarcinoma cell line A549 under the conditions of different concentrations and different action times.

An improved MRS liquid medium was taken as a blank control, the secreted protein of the *Lactobacillus gasseri* obtained in the Embodiment 2 was incubated with a human lung adenocarcinoma cell line A549 at different concentrations (1 μg/ml, 100 μg/ml) and 37° C. for 35 min and 60 min, and then observed under a scanning electron microscope. Results are shown in FIG. 19, where a denotes an incubation result of a cultural supernate without a protein (that is, a supernate removed after precipitation by using saturated ammonium sulfate during separation of a protein crude product by the preparation method of the Embodiment 2), b denotes a result of incubating together with a 1 μg/ml secreted protein of the *Lactobacillus gasseri* for 35 min, c denotes a result of incubating together with a 100 μg/ml secreted protein of the *Lactobacillus gasseri* for 35 min, and d denotes a result of incubating together with a 100 μg/ml secreted protein of the *Lactobacillus gasseri* for 1 h. It can be seen from FIG. 19 that, after being incubated together with 1 μg/ml and 100 μg/ml secreted proteins of the *Lactobacillus gasseri* for 35 min, cell membranes of the A549 had multiple round holes, the integrity of the cell membrane was broken, and a cytopathic effect was more obvious at a protein concentration of 100 μg/ml. It may be seen from diagram d, the cell disrupted and ruptured, became cell debris, and the tumor cell died.

Figure 20:
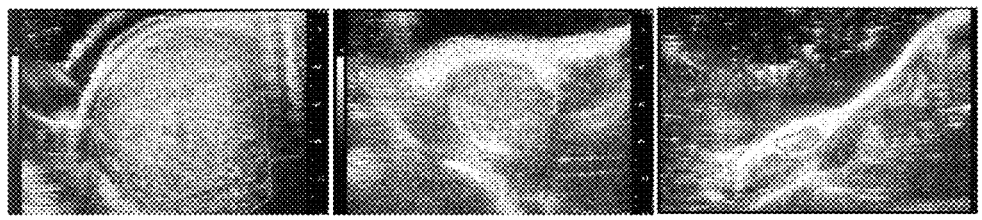
FIG. 20 shows a test result of the secreted protein of the *Lactobacillus gasseri* of the Embodiment 4 of the present disclosure in inhibiting growth of a transplanted tumor.
Figure 21:
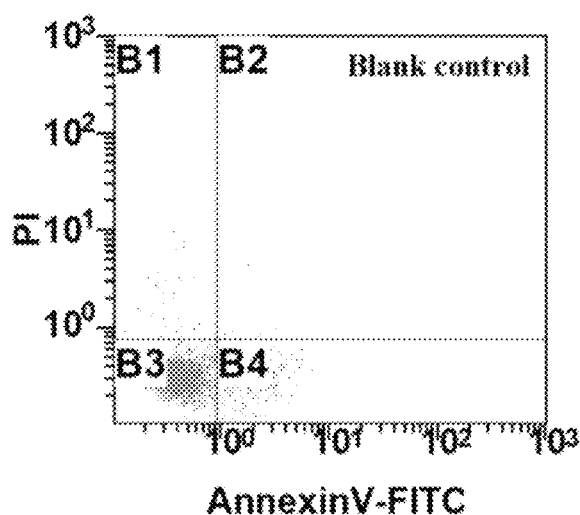
FIG. 21 shows a test result of the secreted protein of the *Lactobacillus gasseri* of the Embodiment 4 of the present disclosure in inducing apoptosis of Hela cells.
Figure 21:
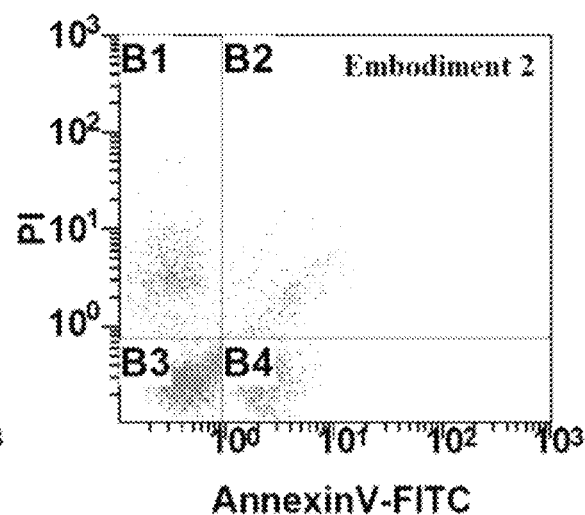
Figure 21:
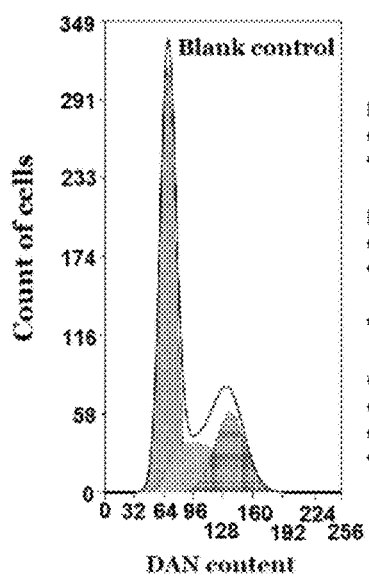
Figure 21:
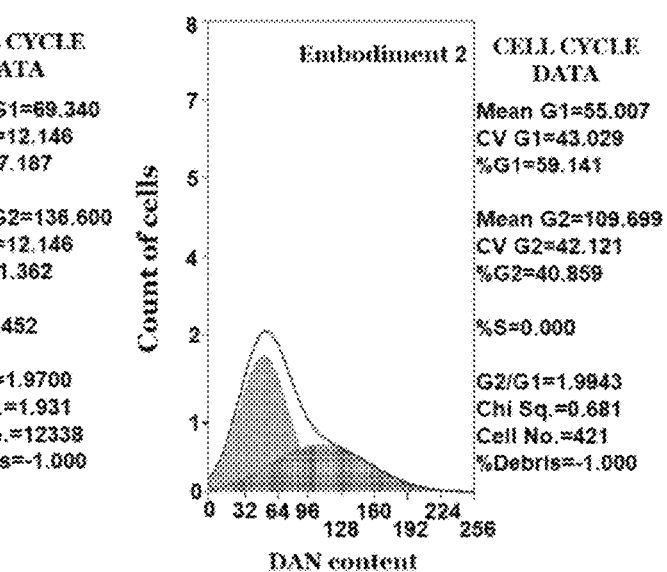

An animal model with a transplanted tumor was constructed, an oncolytic effect in vitro was observed, and results showed that the secreted protein of the *Lactobacillus gasseri* obtained in the Embodiment 2 may significantly inhibited growth of the transplanted tumor (as shown in FIG. 20). Results of a flow cytometer showed that the secreted protein of the *Lactobacillus gasseri* obtained in the Embodiment 2 may induce apoptosis of Hela cells, and had a significant effect on cell cycles of the Hela cells, the Hela cells were treated by using the secreted protein of the *Lactobacillus gasseri* obtained in the Embodiment 2 for 35 min, as shown in FIG. 21, the number of the Hela cells decreased significantly, where a percentage of S-phase cells was reduced to 0%, DNA synthesis of the Hela cells stopped, S phase disappeared, and other phases were affected significantly.

A sequence listing is provided at the end of the application includes a sequence of the *Lactobacillus gasseri* HMV18.

The above description only illustrates preferable embodiments, but is not used to limit the present disclosure, and any modifications, equivalent replacements or improvements made without departing from the spirit and principle of the present disclosure shall all fall within the scope of protection of the present disclosure.

Although embodiments of the present disclosure have been described in detail, it should be understood that various changes, substitutions and alterations can be made herein without departing from the spirit and scope of the disclosure as defined by the appended claims.

Moreover, the scope of the present disclosure is not intended to be limited to the particular embodiments described here. As one of ordinary skill in the art will readily appreciate from the disclosure of the present disclosure that processes, machines, manufacture, compositions of matter, means, methods, or steps, presently existing or later to be developed, may perform substantially the same function or achieve substantially the same result as the corresponding embodiments described herein. Accordingly, the appended claims are intended to include within their scope such processes, machines, manufacture, compositions of matter, means, methods, or steps.

The invention claimed is:

1. A method of treating bacterial or tumor cells, the method comprising contacting the bacterial or tumor cells with Gassericin T of *Lactobacillus gasseri* HMV18, wherein Gassericin T inhibits growth of the bacterial or tumor cells, and wherein Gassericin T is prepared by a preparation method comprising:

step (a), culturing the *Lactobacillus gasseri* HMV18 under an anaerobic condition, and subculturing the *Lactobacillus gasseri* HMV18 to obtain a second-passage bacteria culture;

step (b), centrifuging the second-passage bacteria culture at 5,000 revolutions per minute (rpm) for 10 minutes (min), and removing a precipitate from the centrifuged second-passage bacteria culture to obtain a supernate I;

step (c), adding 1 mole per liter (mol/L) sodium hydroxide (NaOH) and 1 mol/L catalase into the supernate I to obtain a mixture I and adjusting a pH value of the mixture I to be 6.2, stirring the pH-adjusted mixture I at 4° C. for 2 hours (h), allowing the pH-adjusted mixture I to stand for 2 h after stirring before centrifuging the mixture I at 4° C. at 12,000 rpm for 30 min, and removing a precipitate from the centrifuged mixture I to obtain a supernate II; and step (d), adding ammonium sulfate into the supernate II to obtain a mixture II, stirring the mixture II at 4° C. for 2 h, allowing the mixture II to stand for 10 h after stirring before centrifuging the mixture II at 4° C. at 12,000 rpm for 30 min to obtain a centrifuged product, removing a supernate from the centrifuged product to obtain a first product, and collecting a precipitated protein from the first product to obtain Gassericin T of the *Lactobacillus gasseri* HMV18.

2. The method of claim 1, wherein the *Lactobacillus gasseri* HMV18 was deposited in China Center for Type Culture Collection (CCTCC) on Jul. 11, 2019 with a deposit number of CCTCC NO: M 2019538, and a deposit address of Wuhan University, Wuhan, China.

3. The method of claim 1, wherein in step (a), the *Lactobacillus gasseri* HMV18 is cultured under an anaerobic condition at a constant temperature of 37° C. by using an improved de Man, Rogosa and Sharpe (MRS) agar medium, and the improved MRS agar medium comprises the following raw materials in parts by weight: 10 parts of tryptone, 10 parts of beef extract, 5 parts of yeast extract, 20 parts of raffinose, 5 parts of sodium acetate, 2 parts of diamine citrate, 1 part of tween 80, 2 parts of dipotassium phosphate, 0.05 part of manganese sulfate, 0.5 part of magnesium sulfate, 1,000 parts of double distilled water, 15 parts of agar and 0.5 part of L-cysteine hydrochloride.

4. The method of claim 1, wherein in step (a), the *Lactobacillus gasseri* HMV18 is cultured under the anaerobic condition at a constant temperature of 37° C. by using an improved MRS liquid medium, and the improved MRS liquid medium comprises the following raw materials in parts by weight: 10 parts of tryptone, 10 parts of beef extract, 5 parts of yeast extract, 20 parts of raffinose, 5 parts of sodium acetate, 2 parts of diamine citrate, 1 part of tween 80, 2 parts of dipotassium phosphate, 0.05 part of manganese sulfate, 0.5 part of magnesium sulfate and 1,000 parts of double distilled water; and/or wherein step (d) further comprises a step of dialyzing and purifying the centrifuged product.

* * * * *